US007064247B1

(12) United States Patent
Jung

(10) Patent No.: US 7,064,247 B1
(45) Date of Patent: Jun. 20, 2006

(54) NUCLEIC ACID ENCODING MAIZE ENDOPLASMIC RETICULUM OXIDOREDUCTIN AND METHOD OF USE

(75) Inventor: Rudolf Jung, Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 97 days.

(21) Appl. No.: 10/118,101

(22) Filed: Apr. 8, 2002

Related U.S. Application Data

(60) Provisional application No. 60/284,481, filed on Apr. 18, 2001.

(51) Int. Cl.
*A01H 5/00* (2006.01)
*A01H 5/10* (2006.01)
*C12N 15/82* (2006.01)
*C12N 15/53* (2006.01)

(52) U.S. Cl. .................. 800/298; 800/284; 435/419; 536/23.2

(58) Field of Classification Search ............... 800/298, 800/278; 536/23.6; 435/419
See application file for complete search history.

(56) References Cited

OTHER PUBLICATIONS

Walbot, 1999, Accession No. AW000435.*
Colliver et al, 1997, Plant Mol. Biol. 35:509-522.*
Hill et al, 1998, Biochem. Biophys. Res. Comm. 244:573-577.*
Lazar et al, 1988, Mol. Cell. Biol. 8:1247-1252.*
Cabibbo, et al. (2000). *ERO1-L, a Human Protein That Favors Disulfide Bond Formation in the Endoplasmic Reticulum. The Journal of Biological Chemistry*, vol. 275, No. 7, p. 4827-4833.
Cuozzo, et al. (1999). *Competition Between Glutathione and Protein Thiols for Disulphide-bond Formation. Nature Cell Biology*, vol. 1, p. 130-135.
Frand, et al. (2000). *Pathways for Protein Disulphide Bond Formation. Cell Biology*, vol. 10, p. 203-210.
Frand, et al. (1999). *Erolp Oxidizes Protein Disulfide Isomerase in a Pathway for Disulfide Bond Formation in the Endoplasmic Reticulum. Molecular Cell*, vol. 4, p. 469-477.
Pagani, et al. (2000). *Endoplasmic Reticulum Oxidoreductin 1-Lβ(Erol-lβ), a Human Gene Induced in the Course of the Unfolded Protein Response. The Journal of Biological Chemistry*, vol. 275, No. 31, p. 23685-23692.
Pollard, et al. (1998). *Erolp: A Novel and Ubiquitous Protein with an Essential Role in Oxidative Protein Folding in the Endoplasmic Reticulum. Molecular Cell*, vol. 1, p. 171-182.
Walbot, V., Sep. 8, 1999, *Genbank Accession No. AW000435*, Genbank Gi 5847356, *3-4 days old root tissue from Walbot Lab.*

Walbot, V., Dec. 12, 1999, *Genbank Accession No. AW231790*, Genbank Gi 6564168, *Library from developing embryos samples at 14, 21, 28, & 35 days after pollination of the Illinois High Oil Maize Strain Cycle 90.*
Walbot, V., Aug. 9, 1999, *Genbank Accession No. AI943995*, Genbank Gi 5714010, *3-4 days old root tissue from Walbot Lab.*
Cordonnier-Pratt, MM., May 25, 2000, *Genbank Accession No. AW923464*, Genback Gi 8089289, *Library was made from poly-A RNA in the cloning vector lanbda ZAP II. Clones to be sequenced were prepared by mass excision.*
Cordonnier-Pratt, MM., May 25, 2000, *Genbank Accession No. AW923546*, Genbank Gi 8089371, *The library was made from poly-A RNA in the cloning vector lambda ZAP II. Clones to be sequence were prepared by mass excision.*
Michalowski, C.B., Jun. 7, 2000, *Genbank Accession No. BE040220*, Genbank Gi 8335236.
Clark, Bryan, Jan. 3, 2001, *Genbank Accession No. AW448223*, Genbank Gi 12018651.
Anderson, Olin, Aug. 22, 2000, *Genbank Accession No. BE606600*, Genbank Gi 9883764, "Plants were grown in the greenhouse. Spikes at 5, 10, & 15 DAP were harvested, total RNA and poly (A) RNA were prepared, a cDNA library was made, and cDNA clones were in vivo excised to give pBluescript phagemids in the TJ Close lab."
Joudrier, P., Jul. 24, 2000, *Genbank Accession No. BE428450*, Genbank Gi 8426293, "T7 primers used. See Psport1 polylinker site. 0.3-2.0 kbp average insert size."
Lin, X., et al, Oct. 12, 2000, *Genbank Accession No. AAG21499*, Genbank Gi 10645380, "*Arabidopsis thaliana* chromosome 1 BAC T9N14 genomic sequence".
Roundsley, S.D., et al, Mar. 11, 2000, *Genbank Accession No. AAC79609*, Genbank Gi 3928083, "Direct submission".
NCBI Annotation Project et al., Nov. 16, 2000, *Genbank Accession No. XP 002044*, Genbank Gi, 11427251, "Direct submission".
Pagani, M., et al., Nov. 2, 2000, *Genbank Accession No. NP 063944*, Genbank Gi 9845249, "Endoplasmic reticulum oxidoreducatin 1-1beta (ER01—Lbeta), a human gene induced in the course of the unfolded protein response".
Cabibbo,A., et al., Jan. 8, 2002, *Genbank Accession No. NP 056589*, Genbank Gi, 7657067, "Er01—L, a human protein that favors disulfide bond formation in the endoplasmic reticulum".

(Continued)

*Primary Examiner*—Anne Kubelik
(74) *Attorney, Agent, or Firm*—Pioneer Hi-Bred International, Inc.; Kathryn K. Lappegard

(57) ABSTRACT

This invention provides an isolated nucleic acid encoding an endoplasmic reticulum oxidoreductin. The invention also provides recombinant expression cassettes comprising a polynucleotide encoding all or a portion of the endoplasmic reticulum oxidoreductin, wherein expression of the polynucleotide results in production of altered levels of the endoplasmic reticulum oxidoreductin in a transformed plant cell, or plants or seeds regenerated from the transformed cell.

10 Claims, 2 Drawing Sheets

OTHER PUBLICATIONS

Vodkin, L.O., Sep. 21, 2000, *Genbank Accession No. BE820572*, Genbank Gi 10252806, " A Functional Genomics Program for Soybean (NSF 9872565)".

Shoemaker, R., Feb. 7, 2000, *Genbank Accession No. AW396498*, Genbank Gi 6914968, "Public Soybean EST Project".

Shoemaker, R., Nov. 21, 2000, *Genbank Accession No. BF324743*, Genbank Gi 11274390, "Public Soybean EST Project".

Shoemaker, R., Jan. 21, 2000, *Genbank Accession No. AW311228*, Genbank Gi 6726948 "Public Soybean EST Project".

Shoemaker, R., Jul. 28, 2000, *Genbank Accession No. BE473891*, Genbank Gi 9564382, "Public Soybean EST Project".

Shoemaker, R., Mar. 13, 2000, *Genbank Accession No. AW568723*, Genbank Gi 7233376, "Public Soybean EST Project".

Cabibbo, A., et al., Dec. 13, 2001, *Genbank Accession No. NP 055399*, Genbank Gi 7657069, "ERO1—L, a human protein that favors disulfide bond formation in the endoplasmic reticulum."

Nagase, t., et al., Jun. 18, 2002, *Genbank Accession No. AAF06104*, Genbank Gi 6272557, "Prediction of the coding sequences of unidentified human genes. IX. The complete sequences of 100 new cDNA clones from brain which can code for large proteins in vitro."

Cabibbo, A., et al., Feb. 17, 2000, *Genbank Accession No. AAF09172*, Genbank Gi 6456532, "ERO1—L, a human protein that favors disulfide bond formation in the endoplasmic reticulum."

Pagani. M., et al., Nov. 2, 2000, *Genbank Accession No. NP 063944*, Genbank Gi 9845249, "Endoplasmic reticulum oxidoreductin 1-1 beta (ERO1—Lbeta), a human gene induced in the course of the unfolded protein response".

Wing, RA., Aug. 14, 2000, *Genbank Accession No. BE558993*, Genbank Gi 9823483, "Development of a genetically and physically anchored EST resource for barley genomics: Blumeria infected incompatible (Mla6) seedling leaf cDNA library".

Wing, RA.,Dec. 18, 2000, *Genbank Accession No. BF625787*, Genbank Gi 11889521, "Development of a genetically and physically anchored EST resource for barley genomics: Morex cold-stressed seedling shoot cDNA library".

Joudrier, P., Jul. 24, 2000, *Genbank Accession No. BE428450*, Genbank Gi 9426293, "T7 primers used. See pSport1 polyliner site. 0.3-2.0 Kbp average insert size."

Anderson, OA., Jul. 21, 2000, *Genbank Accession No. BE398730*, Genbank Gi 9358204, "Wheat Endosperm Library constructed in Lambda ZAPIII with 8-mer adapter."

Appels, R., Jul. 21, 2000, *Genbank Accession No. BE402137*, Genbank Gi 9361605, "Plants grown in Phytotron with 18C/13C (day/night) 16 hour light."

Lin, X., et al., Oct. 12, 2000, *Genbank Accession No. AC067754*Gnebank Gi 10645366, "*Arabidopsis thaliana* chromosome 1 BAC T9N14 genomic sequence".

Lin, X., Apr. 5, 2000, *Genbank Accession No. AC005770*, Genbank Gi 6598486, "Sequence and analysis of chromosome 2 of the plant *Arabidopsis thaliana*".

* cited by examiner

Fig. 1 Trace modulation of fragment 186.8 in comparison of W64A vs. W64A-fl2. W64A (wild type) is shown in the top graph. W64A-fl2 (mutant) is shown in the bottom graph.
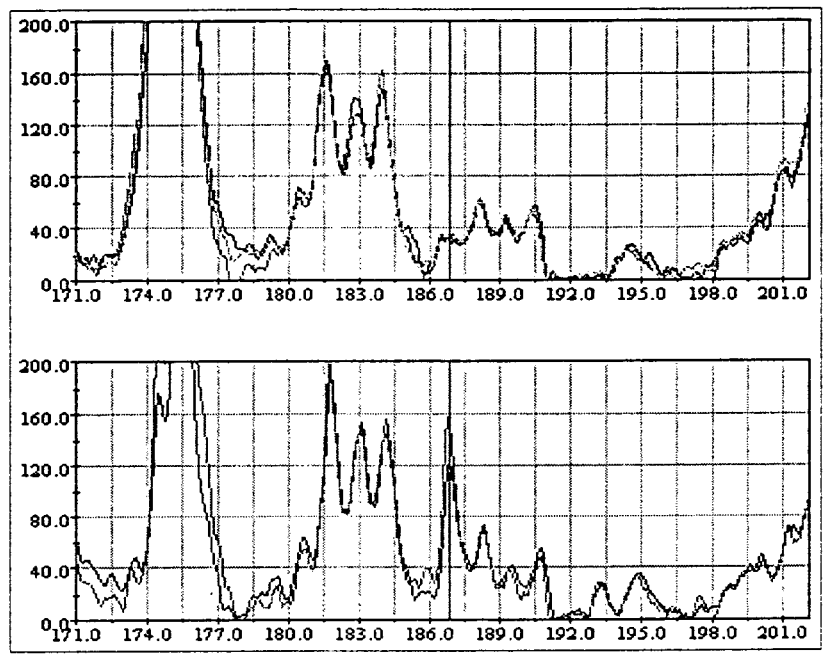
Fig. 2 Confirmation by competitive PCR of the fragment 186.8 as an ERO gene. W64A (wild type) is shown in the top graph. W64A-fl2 (mutant) is shown in the bottom graph. Oligonucleotide primer was ACCGACGATCTGCATGTCCATTG.
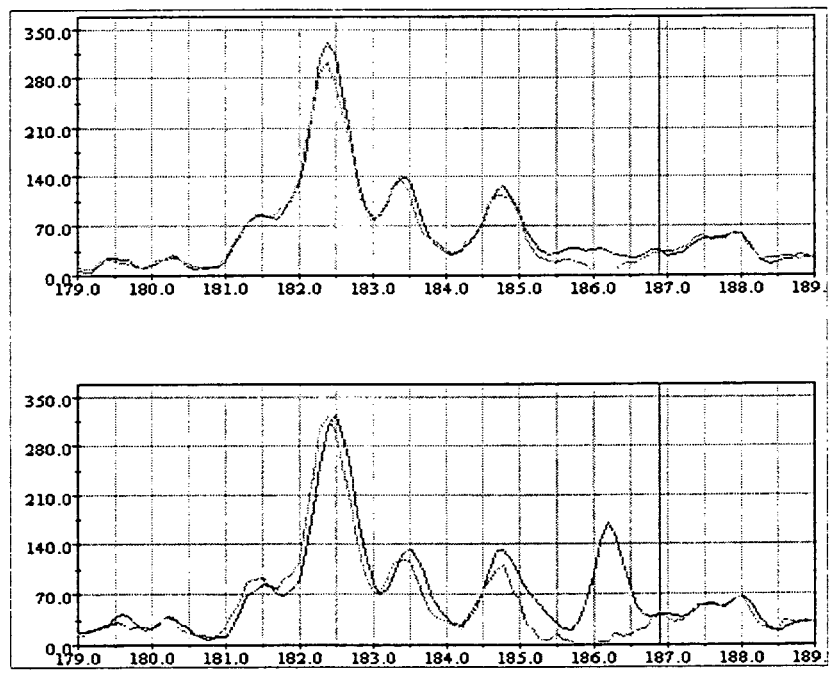

Fig.3 Trace modulation of fragment 301.4 in comparison of W64A vs W64A-Mc. W64A (wild type) is shown in the top graph. W64A –Mc mutant is shown in the bottom graph.
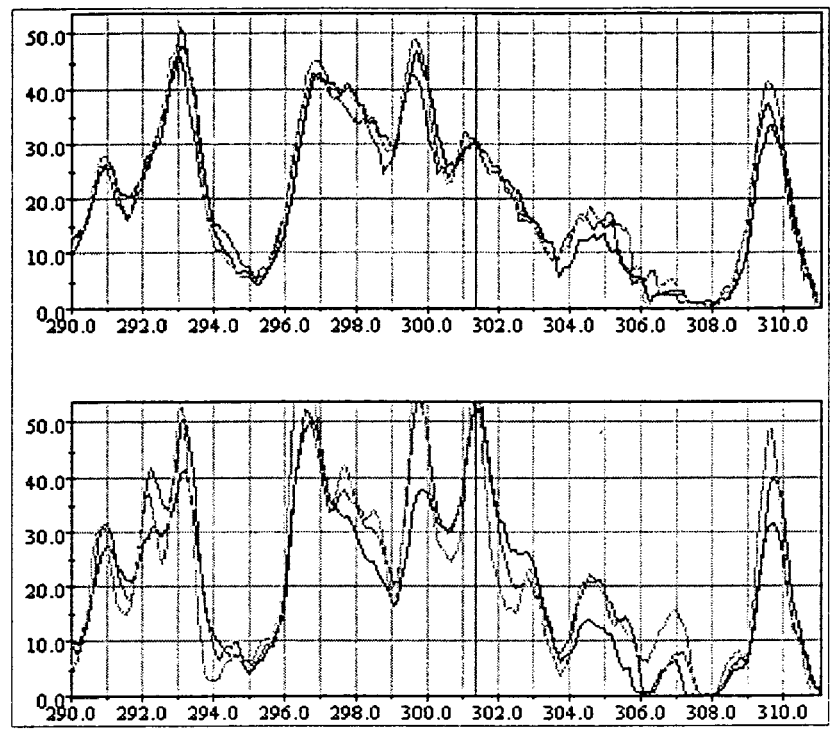
Fig. 4 Confirmation by competitive PCR of the fragment 301.4 as an ERO1 gene. W64A (wild type) is shown in the top graph. W64A –Mc mutant is shown in the bottom graph.
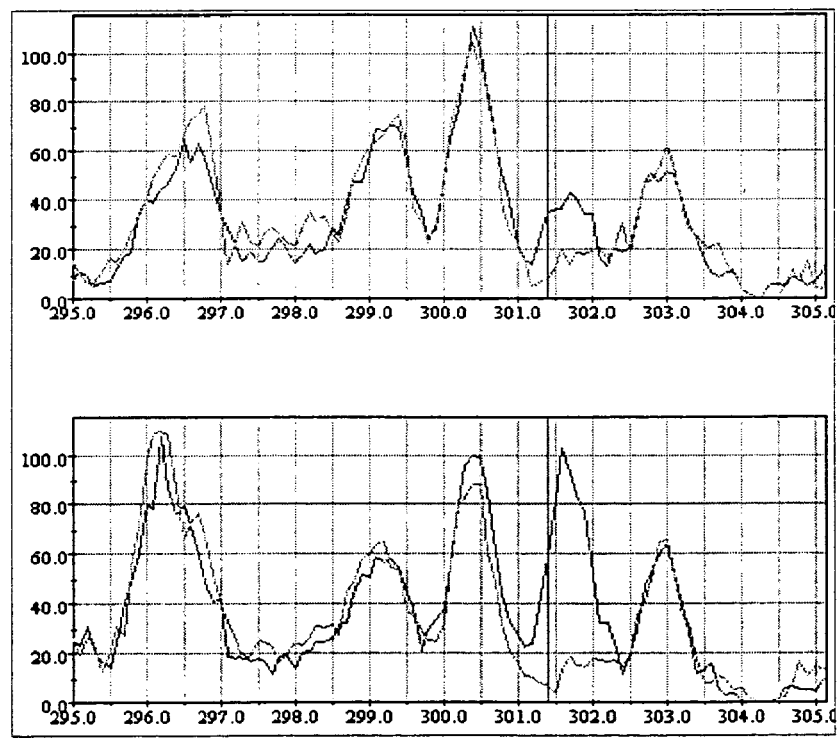

SEQUENCE LISTING

```
<160> NUMBER OF SEQ ID NOS: 11

<210> SEQ ID NO 1
<211> LENGTH: 1866
<212> TYPE: DNA
<213> ORGANISM: zea mays
<220> FEATURE:
<221> NAME/KEY: CDS
<222> LOCATION: (100)...(1519)

<400> SEQUENCE: 1
```

```
ctagactaga ccgaccgcca ccattgcccc cgtgtcttaa cacggggcga aaattccttt      60
cgagatctcg cttctctaag cttccgcggc ggcacggtg atg act atg acc ccc        114
                                           Met Thr Met Thr Pro
                                           1               5 gct ccg gtg gcg aac ggc gca gcg gcc ggc gct ggc ggg ggc atg aag      162
Ala Pro Val Ala Asn Gly Ala Ala Ala Gly Ala Gly Gly Gly Met Lys
                10                  15                  20 cgg cgg ggc ggt agg ttg tgg tac gcg gtc gcc ggt gct ctc ctc gtg      210
Arg Arg Gly Gly Arg Leu Trp Tyr Ala Val Ala Gly Ala Leu Leu Val
            25                  30                  35 gcc ctc ctc gcc gtg gcc gtg agc tac cgc agc ttc ccg ggc gtc cct      258
Ala Leu Leu Ala Val Ala Val Ser Tyr Arg Ser Phe Pro Gly Val Pro
        40                  45                  50 tcc tcc tcc tcg tca cct gga agc tgc ggc tgc cct gct gcg agg aag      306
Ser Ser Ser Ser Ser Pro Gly Ser Cys Gly Cys Pro Ala Ala Arg Lys
    55                  60                  65 tac acg ggg atg gtg gag gac tgc tgc tgc gac tat gag acg gtg gac      354
Tyr Thr Gly Met Val Glu Asp Cys Cys Cys Asp Tyr Glu Thr Val Asp
70                  75                  80                  85 gcc atc aac gag gag gtc ctg cat cca atc cta cag gaa ctc gtt aag      402
Ala Ile Asn Glu Glu Val Leu His Pro Ile Leu Gln Glu Leu Val Lys
                90                  95                  100 ttg ccc ttc ttc agg tac ttc aag gtt aaa ttg tgg tgt gac tgc cct      450
Leu Pro Phe Phe Arg Tyr Phe Lys Val Lys Leu Trp Cys Asp Cys Pro
            105                 110                 115 ttt tgg ccc gat gat gga atg tgc aag ctt aga gat tgt agt gtt tgt      498
Phe Trp Pro Asp Asp Gly Met Cys Lys Leu Arg Asp Cys Ser Val Cys
        120                 125                 130 gag tgt ccg gag aat gag ttc cct gaa cca ttc agg aaa cct tac aat      546
Glu Cys Pro Glu Asn Glu Phe Pro Glu Pro Phe Arg Lys Pro Tyr Asn
    135                 140                 145 gga ctt tct cca gat agt atg atg tgc caa gaa gga aaa ccc cag gct      594
Gly Leu Ser Pro Asp Ser Met Met Cys Gln Glu Gly Lys Pro Gln Ala
150                 155                 160                 165 gcc gtt gat aaa act ctt gac agc aag gtt ttc aaa gga tgg gtt gaa      642
Ala Val Asp Lys Thr Leu Asp Ser Lys Val Phe Lys Gly Trp Val Glu
                170                 175                 180 act gac aat ccg tgg aca tct gat gac gag act gat aat aat gag atg      690
Thr Asp Asn Pro Trp Thr Ser Asp Asp Glu Thr Asp Asn Asn Glu Met
            185                 190                 195 act tac gtg aat ctt caa ctg aat cct gaa cga tac act ggc tat act      738
Thr Tyr Val Asn Leu Gln Leu Asn Pro Glu Arg Tyr Thr Gly Tyr Thr
        200                 205                 210 ggt gat tca gca aga aga ata tgg gac gct att tac aaa gag aac tgt      786
Gly Asp Ser Ala Arg Arg Ile Trp Asp Ala Ile Tyr Lys Glu Asn Cys
    215                 220                 225 cca aaa tat ccc tct gaa gaa ctg tgc cat gag aag aag gca ttg tac      834
Pro Lys Tyr Pro Ser Glu Glu Leu Cys His Glu Lys Lys Ala Leu Tyr
230                 235                 240                 245 aag ctt att tca gga ttg cac tcc tca att tca gtg cat att gct tat      882
Lys Leu Ile Ser Gly Leu His Ser Ser Ile Ser Val His Ile Ala Tyr
                250                 255                 260 gat tac ctt ctt gat gaa tct act aac tca tgg gga caa aat ctt cct      930
Asp Tyr Leu Leu Asp Glu Ser Thr Asn Ser Trp Gly Gln Asn Leu Pro
            265                 270                 275 ttg ttg tat gac cgc gtc ctg aag tac cca gaa cgt gtc cag aat ctg      978
Leu Leu Tyr Asp Arg Val Leu Lys Tyr Pro Glu Arg Val Gln Asn Leu
        280                 285                 290
```

```
tac ttc acc tac ctg ttt gtt ctt cgg gcc gtg aca aag gca gca aat      1026
Tyr Phe Thr Tyr Leu Phe Val Leu Arg Ala Val Thr Lys Ala Ala Asn
295                 300                 305 tat ctt gag cag gct gag tac aat acc ggc aat cct gaa gac gac ttg      1074
Tyr Leu Glu Gln Ala Glu Tyr Asn Thr Gly Asn Pro Glu Asp Asp Leu
310                 315                 320                 325 aaa aca gaa tct ctt gtg aag cag ttg ctt tac aat tcc aag tta aga      1122
Lys Thr Glu Ser Leu Val Lys Gln Leu Leu Tyr Asn Ser Lys Leu Arg
            330                 335                 340 tct gca tgt cca ttg cct ttt gat gaa gcc aaa ctt tgg caa ggc gaa      1170
Ser Ala Cys Pro Leu Pro Phe Asp Glu Ala Lys Leu Trp Gln Gly Glu
        345                 350                 355 aat ggt cct gag cta aag caa gag att cag aag caa ttt aga aac att      1218
Asn Gly Pro Glu Leu Lys Gln Glu Ile Gln Lys Gln Phe Arg Asn Ile
    360                 365                 370 agt gca att atg gac tgt gtt gga tgc gag aag tgc cga ctg tgg gga      1266
Ser Ala Ile Met Asp Cys Val Gly Cys Glu Lys Cys Arg Leu Trp Gly
375                 380                 385 aag ctc caa gtt cat ggt ctt gga act gca ctg aaa att ctt ttc tct      1314
Lys Leu Gln Val His Gly Leu Gly Thr Ala Leu Lys Ile Leu Phe Ser
390                 395                 400                 405 gtt gat ggg gac agc cat atg aat cag cca ttg cag ctg cag cga aat      1362
Val Asp Gly Asp Ser His Met Asn Gln Pro Leu Gln Leu Gln Arg Asn
            410                 415                 420 gag gtc att gca ttg ttc aat ctt ctg aac agg ctc tca gag tct gtc      1410
Glu Val Ile Ala Leu Phe Asn Leu Leu Asn Arg Leu Ser Glu Ser Val
        425                 430                 435 aaa ttt gta cat gaa aaa gga tca tca att gaa gaa gtc att gag gaa      1458
Lys Phe Val His Glu Lys Gly Ser Ser Ile Glu Glu Val Ile Glu Glu
    440                 445                 450 cag atc cct tca acg gtt caa aag agt gtt tcc atg ccg aat ctt aaa      1506
Gln Ile Pro Ser Thr Val Gln Lys Ser Val Ser Met Pro Asn Leu Lys
455                 460                 465 ctg gac ttc ctc t gagatgtatg agagtaattt gtagttatac aagattgcaa        1559
Leu Asp Phe Leu
470 tgacatgctg gaagattaac atagacatgt acggatataa cgaaagatta acatgtgctg   1619 gaagcagttt catacatact tgtgttgcag ctgtatttaa gagaatgaga gatacagata   1679 cttttgagct aaatgcgatg acacagttaa catagccccc ccgcacctca aacttttccg   1739 tgtatagggt tcctccgctg taaatcaaag gatgtcaccc ctctgcactc gccatgatca   1799 agagaatatt ctcgctcaac ttgatcacct gaccacgaaa caggtagcga gcaaattttt   1859 tttgtcc                                                             1866

<210> SEQ ID NO 2
<211> LENGTH: 473
<212> TYPE: PRT
<213> ORGANISM: zea mays

<400> SEQUENCE: 2

Met Thr Met Thr Pro Ala Pro Val Ala Asn Gly Ala Ala Gly Ala
1               5                   10                  15

Gly Gly Gly Met Lys Arg Arg Gly Gly Arg Leu Trp Tyr Ala Val Ala
            20                  25                  30

Gly Ala Leu Leu Val Ala Leu Leu Ala Val Ala Val Ser Tyr Arg Ser
        35                  40                  45

Phe Pro Gly Val Pro Ser Ser Ser Ser Pro Gly Ser Cys Gly Cys
50                  55                  60
```

-continued

```
Pro Ala Ala Arg Lys Tyr Thr Gly Met Val Glu Asp Cys Cys Asp
65                  70                  75                  80

Tyr Glu Thr Val Asp Ala Ile Asn Glu Glu Val Leu His Pro Ile Leu
                85                  90                  95

Gln Glu Leu Val Lys Leu Pro Phe Phe Arg Tyr Phe Lys Val Lys Leu
            100                 105                 110

Trp Cys Asp Cys Pro Phe Trp Pro Asp Asp Gly Met Cys Lys Leu Arg
            115                 120                 125

Asp Cys Ser Val Cys Glu Cys Pro Glu Asn Glu Phe Pro Glu Pro Phe
            130                 135                 140

Arg Lys Pro Tyr Asn Gly Leu Ser Pro Asp Ser Met Met Cys Gln Glu
145                 150                 155                 160

Gly Lys Pro Gln Ala Ala Val Asp Lys Thr Leu Asp Ser Lys Val Phe
                165                 170                 175

Lys Gly Trp Val Glu Thr Asp Asn Pro Trp Thr Ser Asp Asp Glu Thr
            180                 185                 190

Asp Asn Asn Glu Met Thr Tyr Val Asn Leu Gln Leu Asn Pro Glu Arg
            195                 200                 205

Tyr Thr Gly Tyr Thr Gly Asp Ser Ala Arg Arg Ile Trp Asp Ala Ile
210                 215                 220

Tyr Lys Glu Asn Cys Pro Lys Tyr Pro Ser Glu Glu Leu Cys His Glu
225                 230                 235                 240

Lys Lys Ala Leu Tyr Lys Leu Ile Ser Gly Leu His Ser Ser Ile Ser
                245                 250                 255

Val His Ile Ala Tyr Asp Tyr Leu Leu Asp Glu Ser Thr Asn Ser Trp
            260                 265                 270

Gly Gln Asn Leu Pro Leu Leu Tyr Asp Arg Val Leu Lys Tyr Pro Glu
            275                 280                 285

Arg Val Gln Asn Leu Tyr Phe Thr Tyr Leu Phe Val Leu Arg Ala Val
            290                 295                 300

Thr Lys Ala Ala Asn Tyr Leu Glu Gln Ala Glu Tyr Asn Thr Gly Asn
305                 310                 315                 320

Pro Glu Asp Asp Leu Lys Thr Glu Ser Leu Val Lys Gln Leu Leu Tyr
                325                 330                 335

Asn Ser Lys Leu Arg Ser Ala Cys Pro Leu Pro Phe Asp Glu Ala Lys
            340                 345                 350

Leu Trp Gln Gly Glu Asn Gly Pro Glu Leu Lys Gln Glu Ile Gln Lys
            355                 360                 365

Gln Phe Arg Asn Ile Ser Ala Ile Met Asp Cys Val Gly Cys Glu Lys
            370                 375                 380

Cys Arg Leu Trp Gly Lys Leu Gln Val His Gly Leu Gly Thr Ala Leu
385                 390                 395                 400

Lys Ile Leu Phe Ser Val Asp Gly Asp Ser His Met Asn Gln Pro Leu
                405                 410                 415

Gln Leu Gln Arg Asn Glu Val Ile Ala Leu Phe Asn Leu Leu Asn Arg
            420                 425                 430

Leu Ser Glu Ser Val Lys Phe Val His Glu Lys Gly Ser Ser Ile Glu
            435                 440                 445

Glu Val Ile Glu Glu Gln Ile Pro Ser Thr Val Gln Lys Ser Val Ser
            450                 455                 460

Met Pro Asn Leu Lys Leu Asp Phe Leu
465                 470
```

```
<210> SEQ ID NO 3
<211> LENGTH: 1085
<212> TYPE: DNA
<213> ORGANISM: zea mays
<220> FEATURE:
<221> NAME/KEY: CDS
<222> LOCATION: (3)...(846)

<400> SEQUENCE: 3 ct gat aat aat gag atg act tac gtg aat ctt caa ctg aat cct gaa        47
   Asp Asn Asn Glu Met Thr Tyr Val Asn Leu Gln Leu Asn Pro Glu
    1               5                  10                  15 cga tac act ggc tat acc ggt gat tca gca agg agg ata tgg gat gct       95
Arg Tyr Thr Gly Tyr Thr Gly Asp Ser Ala Arg Arg Ile Trp Asp Ala
                 20                  25                  30 att tat aaa gag aac tgt cca aaa tat ccc tct gaa gaa ctg tgc cat      143
Ile Tyr Lys Glu Asn Cys Pro Lys Tyr Pro Ser Glu Glu Leu Cys His
             35                  40                  45 gag aag aag gta ttg tac aag ctt att tca ggg ttg cac tcc tca atc      191
Glu Lys Lys Val Leu Tyr Lys Leu Ile Ser Gly Leu His Ser Ser Ile
         50                  55                  60 tcg gtg cat att gct tat gat tac ctt ctt gat gaa tct act aac tca      239
Ser Val His Ile Ala Tyr Asp Tyr Leu Leu Asp Glu Ser Thr Asn Ser
     65                  70                  75 tgg gga caa aat ctt tct ttg ctg tat gac cgt gtc ctg aag tac cca      287
Trp Gly Gln Asn Leu Ser Leu Leu Tyr Asp Arg Val Leu Lys Tyr Pro
 80                  85                  90                  95 gaa cgt gtc cag aat cta tac ttc acc tac ctg ttt gtt ctt cga gcc      335
Glu Arg Val Gln Asn Leu Tyr Phe Thr Tyr Leu Phe Val Leu Arg Ala
                100                 105                 110 gtg aca aag gca gca gat tat ctt gag cag gct gag tac aat act ggc      383
Val Thr Lys Ala Ala Asp Tyr Leu Glu Gln Ala Glu Tyr Asn Thr Gly
            115                 120                 125 aat cct gaa gat gac ttg aaa aca gaa tct ctt gtg aag caa ttg ctt      431
Asn Pro Glu Asp Asp Leu Lys Thr Glu Ser Leu Val Lys Gln Leu Leu
        130                 135                 140 tac aat tcc aag tta aga tct gca tgt cca ttg cct ttt gat gaa gcc      479
Tyr Asn Ser Lys Leu Arg Ser Ala Cys Pro Leu Pro Phe Asp Glu Ala
    145                 150                 155 aaa ctc tgg caa ggt gaa aat ggt cct gag cta aag caa gag att cag      527
Lys Leu Trp Gln Gly Glu Asn Gly Pro Glu Leu Lys Gln Glu Ile Gln
160                 165                 170                 175 aag caa ttt aga aat att agt gca att atg gac tgt gtt gga tgc gag      575
Lys Gln Phe Arg Asn Ile Ser Ala Ile Met Asp Cys Val Gly Cys Glu
                180                 185                 190 aag tgc cga ctg tgg gga aag ctc caa gtt ctt ggc ctt gga act gct      623
Lys Cys Arg Leu Trp Gly Lys Leu Gln Val Leu Gly Leu Gly Thr Ala
            195                 200                 205 ctg aaa att ctt ttc tcc gtt gat gga gac agc cat ttg aat cag ccg      671
Leu Lys Ile Leu Phe Ser Val Asp Gly Asp Ser His Leu Asn Gln Pro
        210                 215                 220 ttg cag ctg cag cga aat gag gtc att gca ttg ttc aat ctt ctg aac      719
Leu Gln Leu Gln Arg Asn Glu Val Ile Ala Leu Phe Asn Leu Leu Asn
    225                 230                 235 agg ctc tca gag tct gtc aaa ttt gta cat gaa aaa gga tca tca gtc      767
Arg Leu Ser Glu Ser Val Lys Phe Val His Glu Lys Gly Ser Ser Val
240                 245                 250                 255 gaa gaa gtc atc aac gaa cag agc cct tca act gtt caa aag ggt gct      815
Glu Glu Val Ile Asn Glu Gln Ser Pro Ser Thr Val Gln Lys Gly Ala
                260                 265                 270
```

```
tcc aag acg aat ctt aaa ctg gac ttc ctc t gagatgtaag ggtgtaattt        866
Ser Lys Thr Asn Leu Lys Leu Asp Phe Leu
            275                 280 gtagttatag aaggacacgc tggaagatta acatagatat gcacggatat accgaaagat       926
taacatgcgc tggccgtacg tactttgttg caaagagata caaaccctttt ttagctaaat      986 gtgatgccac agttaaccaa atatacagct agagaactaa gggtatgtac aatgatgttt       1046
aatgtagtct tttaaggtgt ttaaaggggg gcatttgca                              1085

<210> SEQ ID NO 4
<211> LENGTH: 281
<212> TYPE: PRT
<213> ORGANISM: zea mays

<400> SEQUENCE: 4

Asp Asn Asn Glu Met Thr Tyr Val Asn Leu Gln Leu Asn Pro Glu Arg
 1               5                  10                  15

Tyr Thr Gly Tyr Thr Gly Asp Ser Ala Arg Arg Ile Trp Asp Ala Ile
                20                  25                  30

Tyr Lys Glu Asn Cys Pro Lys Tyr Pro Ser Glu Glu Leu Cys His Glu
            35                  40                  45

Lys Lys Val Leu Tyr Lys Leu Ile Ser Gly Leu His Ser Ser Ile Ser
        50                  55                  60

Val His Ile Ala Tyr Asp Tyr Leu Leu Asp Glu Ser Thr Asn Ser Trp
 65                 70                  75                  80

Gly Gln Asn Leu Ser Leu Leu Tyr Asp Arg Val Leu Lys Tyr Pro Glu
                85                  90                  95

Arg Val Gln Asn Leu Tyr Phe Thr Tyr Leu Phe Val Leu Arg Ala Val
               100                 105                 110

Thr Lys Ala Ala Asp Tyr Leu Glu Gln Ala Glu Tyr Asn Thr Gly Asn
           115                 120                 125

Pro Glu Asp Asp Leu Lys Thr Glu Ser Leu Val Lys Gln Leu Leu Tyr
       130                 135                 140

Asn Ser Lys Leu Arg Ser Ala Cys Pro Leu Pro Phe Asp Glu Ala Lys
145                 150                 155                 160

Leu Trp Gln Gly Glu Asn Gly Pro Glu Leu Lys Gln Glu Ile Gln Lys
                165                 170                 175

Gln Phe Arg Asn Ile Ser Ala Ile Met Asp Cys Val Gly Cys Glu Lys
            180                 185                 190

Cys Arg Leu Trp Gly Lys Leu Gln Val Leu Gly Leu Gly Thr Ala Leu
        195                 200                 205

Lys Ile Leu Phe Ser Val Asp Gly Asp Ser His Leu Asn Gln Pro Leu
    210                 215                 220

Gln Leu Gln Arg Asn Glu Val Ile Ala Leu Phe Asn Leu Leu Asn Arg
225                 230                 235                 240

Leu Ser Glu Ser Val Lys Phe Val His Glu Lys Gly Ser Ser Val Glu
                245                 250                 255

Glu Val Ile Asn Glu Gln Ser Pro Ser Thr Val Gln Lys Gly Ala Ser
            260                 265                 270

Lys Thr Asn Leu Lys Leu Asp Phe Leu
        275                 280

<210> SEQ ID NO 5
<211> LENGTH: 1560
<212> TYPE: DNA
<213> ORGANISM: Glycine max
```

```
<220> FEATURE:
<221> NAME/KEY: CDS
<222> LOCATION: (62)...(1457)

<400> SEQUENCE: 5
tctgggtctg tgaaaagctc ggtgctttgt ttcggaagca ccgacattgg gtaacagtgt         60 g atg gtg aaa tcg gag att gag aag aag ggt tgc agc aca aga caa tgg        109
  Met Val Lys Ser Glu Ile Glu Lys Lys Gly Cys Ser Thr Arg Gln Trp
   1               5                  10                  15 ctt tgg ctg gtg atg gct ctc gtc gct gtt ttt gtt gcc atg gcc atg          157
Leu Trp Leu Val Met Ala Leu Val Ala Val Phe Val Ala Met Ala Met
                 20                  25                  30 tct tcc aaa acc tct cca aaa gct ctg ttt gga gcc att gat aga gct          205
Ser Ser Lys Thr Ser Pro Lys Ala Leu Phe Gly Ala Ile Asp Arg Ala
         35                  40                  45 tgt ccg tgt gct cgg ggc aca ccg aag tac agt ggc atg gtg gag gat          253
Cys Pro Cys Ala Arg Gly Thr Pro Lys Tyr Ser Gly Met Val Glu Asp
 50                  55                  60 tgt tgt tgt gat tat gaa act gtg gat cgt ctt aat gaa gaa gtg ttg          301
Cys Cys Cys Asp Tyr Glu Thr Val Asp Arg Leu Asn Glu Glu Val Leu
 65                  70                  75                  80 cac cct tcc ctc cag gag ctc gtg aag acc cct ttc ttt cga tat ttt          349
His Pro Ser Leu Gln Glu Leu Val Lys Thr Pro Phe Phe Arg Tyr Phe
                 85                  90                  95 aag gtg aag tta tgg tgt gac tgc cct ttc tgg cct gat gat ggc atg          397
Lys Val Lys Leu Trp Cys Asp Cys Pro Phe Trp Pro Asp Asp Gly Met
            100                 105                 110 tgt cgg ttg cgg gac tgt agt gtg tgt gaa tgc cct gaa aat gaa ttc          445
Cys Arg Leu Arg Asp Cys Ser Val Cys Glu Cys Pro Glu Asn Glu Phe
        115                 120                 125 ccc gaa tca ttt aag aag cct gac cgt cgc ctt tca atg act gat ctt          493
Pro Glu Ser Phe Lys Lys Pro Asp Arg Arg Leu Ser Met Thr Asp Leu
130                 135                 140 gtt tgt caa gaa gga aaa cct cag gca gcc gtt gac cgt act tta gac          541
Val Cys Gln Glu Gly Lys Pro Gln Ala Ala Val Asp Arg Thr Leu Asp
145                 150                 155                 160 agt aaa gct ttc aga gga tgg aca gaa ata gac aat cca tgg aca aat          589
Ser Lys Ala Phe Arg Gly Trp Thr Glu Ile Asp Asn Pro Trp Thr Asn
                165                 170                 175 gat gat gag act gac aat gat gag atg aca tac gtg aat ctt caa ctg          637
Asp Asp Glu Thr Asp Asn Asp Glu Met Thr Tyr Val Asn Leu Gln Leu
            180                 185                 190 aat ccg gaa aga tat act ggt tac act ggt cca tct gca aga agg ata          685
Asn Pro Glu Arg Tyr Thr Gly Tyr Thr Gly Pro Ser Ala Arg Arg Ile
        195                 200                 205 tgg gat gct gtc tac tct gag aac tgc ccc aaa tat ccg tct cag gag          733
Trp Asp Ala Val Tyr Ser Glu Asn Cys Pro Lys Tyr Pro Ser Gln Glu
210                 215                 220 tta tgc caa gag gaa aag att ttg tat aaa ttg ata tct ggt ctt cac          781
Leu Cys Gln Glu Glu Lys Ile Leu Tyr Lys Leu Ile Ser Gly Leu His
225                 230                 235                 240 tcc tcc ata tca att cat ata gct tct gat tat cta ctt gag gaa gct          829
Ser Ser Ile Ser Ile His Ile Ala Ser Asp Tyr Leu Leu Glu Glu Ala
                245                 250                 255 aca aat ttg tgg gga caa aat ctt act ttg atg tat gac cga gtc cta          877
Thr Asn Leu Trp Gly Gln Asn Leu Thr Leu Met Tyr Asp Arg Val Leu
            260                 265                 270 aga tac cct gat cgt gtc aga aat ttg tat ttc act ttt ctc ttt gtt          925
Arg Tyr Pro Asp Arg Val Arg Asn Leu Tyr Phe Thr Phe Leu Phe Val
        275                 280                 285
```

```
ctg cga gca gta acc aaa gct tca gat tat ctg gaa cag gca gag tat      973
Leu Arg Ala Val Thr Lys Ala Ser Asp Tyr Leu Glu Gln Ala Glu Tyr
    290                 295                 300 gat act ggt aac ccc aat gag gac ctt aca aca caa tcc ttg ata aaa     1021
Asp Thr Gly Asn Pro Asn Glu Asp Leu Thr Thr Gln Ser Leu Ile Lys
305                 310                 315                 320 cag cta ctt tac aac ccc aag ctt caa gct gca tgt cca att cca ttt     1069
Gln Leu Leu Tyr Asn Pro Lys Leu Gln Ala Ala Cys Pro Ile Pro Phe
                325                 330                 335 gat gaa gct aat ttg tgg aaa ggg caa agt gga cct gag cta aaa cag     1117
Asp Glu Ala Asn Leu Trp Lys Gly Gln Ser Gly Pro Glu Leu Lys Gln
            340                 345                 350 aaa att caa caa caa ttc aga aac atc agt gca ttg atg gat tgt gta     1165
Lys Ile Gln Gln Gln Phe Arg Asn Ile Ser Ala Leu Met Asp Cys Val
        355                 360                 365 gga tgt gag aaa tgt cga tta tgg ggt aag ctt cag gtt ctt ggt ctt     1213
Gly Cys Glu Lys Cys Arg Leu Trp Gly Lys Leu Gln Val Leu Gly Leu
    370                 375                 380 gga act gca tta aag att ctc ttc tct gtt gat ggt caa gaa aac tcg     1261
Gly Thr Ala Leu Lys Ile Leu Phe Ser Val Asp Gly Gln Glu Asn Ser
385                 390                 395                 400 agt cat aca ctg cag ctg caa agg aat gag gta att gca ttg acg aac     1309
Ser His Thr Leu Gln Leu Gln Arg Asn Glu Val Ile Ala Leu Thr Asn
                405                 410                 415 ctt ctt aat cga ctc tcg gaa tcc gtc aaa ttc gtc cac gaa gtg gga     1357
Leu Leu Asn Arg Leu Ser Glu Ser Val Lys Phe Val His Glu Val Gly
            420                 425                 430 cct aca gct gaa aga atc atg gaa gga gga cat ttt tct gct cat aca     1405
Pro Thr Ala Glu Arg Ile Met Glu Gly Gly His Phe Ser Ala His Thr
        435                 440                 445 aga aca ctg att agc tca tgg aaa aaa att tgg tcc tat gta tct aaa     1453
Arg Thr Leu Ile Ser Ser Trp Lys Lys Ile Trp Ser Tyr Val Ser Lys
    450                 455                 460 act t aggtaacatg ctctcttctg agtatttgtc atatttctcg tttgttgtac         1507
Thr
465 caaactgagt attacatgtt tgcaatctgc aagctataat tggttacagt tca           1560

<210> SEQ ID NO 6
<211> LENGTH: 465
<212> TYPE: PRT
<213> ORGANISM: Glycine max

<400> SEQUENCE: 6

Met Val Lys Ser Glu Ile Glu Lys Lys Gly Cys Ser Thr Arg Gln Trp
1               5                   10                  15

Leu Trp Leu Val Met Ala Leu Ala Val Phe Val Ala Met Ala Met
            20                  25                  30

Ser Ser Lys Thr Ser Pro Lys Ala Leu Phe Gly Ala Ile Asp Arg Ala
        35                  40                  45

Cys Pro Cys Ala Arg Gly Thr Pro Lys Tyr Ser Gly Met Val Glu Asp
    50                  55                  60

Cys Cys Cys Asp Tyr Glu Thr Val Asp Arg Leu Asn Glu Glu Val Leu
65                  70                  75                  80

His Pro Ser Leu Gln Glu Leu Val Lys Thr Pro Phe Arg Tyr Phe
                85                  90                  95

Lys Val Lys Leu Trp Cys Asp Cys Pro Phe Trp Pro Asp Asp Gly Met
            100                 105                 110
```

```
Cys Arg Leu Arg Asp Cys Ser Val Cys Glu Cys Pro Glu Asn Glu Phe
            115                 120                 125

Pro Glu Ser Phe Lys Lys Pro Asp Arg Arg Leu Ser Met Thr Asp Leu
        130                 135                 140

Val Cys Gln Glu Gly Lys Pro Gln Ala Ala Val Asp Arg Thr Leu Asp
145                 150                 155                 160

Ser Lys Ala Phe Arg Gly Trp Thr Glu Ile Asp Asn Pro Trp Thr Asn
                165                 170                 175

Asp Asp Glu Thr Asp Asn Asp Glu Met Thr Tyr Val Asn Leu Gln Leu
            180                 185                 190

Asn Pro Glu Arg Tyr Thr Gly Tyr Thr Gly Pro Ser Ala Arg Arg Ile
        195                 200                 205

Trp Asp Ala Val Tyr Ser Glu Asn Cys Pro Lys Tyr Pro Ser Gln Glu
210                 215                 220

Leu Cys Gln Glu Glu Lys Ile Leu Tyr Lys Leu Ile Ser Gly Leu His
225                 230                 235                 240

Ser Ser Ile Ser Ile His Ile Ala Ser Asp Tyr Leu Leu Glu Glu Ala
                245                 250                 255

Thr Asn Leu Trp Gly Gln Asn Leu Thr Leu Met Tyr Asp Arg Val Leu
            260                 265                 270

Arg Tyr Pro Asp Arg Val Arg Asn Leu Tyr Phe Thr Phe Leu Phe Val
        275                 280                 285

Leu Arg Ala Val Thr Lys Ala Ser Asp Tyr Leu Glu Gln Ala Glu Tyr
290                 295                 300

Asp Thr Gly Asn Pro Asn Glu Asp Leu Thr Thr Gln Ser Leu Ile Lys
305                 310                 315                 320

Gln Leu Leu Tyr Asn Pro Lys Leu Gln Ala Ala Cys Pro Ile Pro Phe
                325                 330                 335

Asp Glu Ala Asn Leu Trp Lys Gly Gln Ser Gly Pro Glu Leu Lys Gln
            340                 345                 350

Lys Ile Gln Gln Gln Phe Arg Asn Ile Ser Ala Leu Met Asp Cys Val
        355                 360                 365

Gly Cys Glu Lys Cys Arg Leu Trp Gly Lys Leu Gln Val Leu Gly Leu
370                 375                 380

Gly Thr Ala Leu Lys Ile Leu Phe Ser Val Asp Gly Gln Glu Asn Ser
385                 390                 395                 400

Ser His Thr Leu Gln Leu Gln Arg Asn Glu Val Ile Ala Leu Thr Asn
                405                 410                 415

Leu Leu Asn Arg Leu Ser Glu Ser Val Lys Phe Val His Glu Val Gly
            420                 425                 430

Pro Thr Ala Glu Arg Ile Met Glu Gly Gly His Phe Ser Ala His Thr
        435                 440                 445

Arg Thr Leu Ile Ser Ser Trp Lys Lys Ile Trp Ser Tyr Val Ser Lys
        450                 455                 460

Thr
465

<210> SEQ ID NO 7
<211> LENGTH: 440
<212> TYPE: DNA
<213> ORGANISM: Glycine max
<220> FEATURE:
<221> NAME/KEY: CDS
<222> LOCATION: (133)...(438)
<220> FEATURE:
```

<221> NAME/KEY: misc_feature
<222> LOCATION: (1)...(440)
<223> OTHER INFORMATION: n = A,T,C or G

<400> SEQUENCE: 7

```
caaanatctc gtcttttcgc gtttccgttg gtggttttc gttttcctca gtgttccttc      60
agtgattttc ttctgggtct gtgaaaagct cggtgctttg tttcggaagc accgacattg    120
gggaactgtg tg atg gtg aaa gcg gag att gag aaa aag ggt tgc agc aca    171
              Met Val Lys Ala Glu Ile Glu Lys Lys Gly Cys Ser Thr
                1               5                  10 aga cga tgg ctt tgg ctt gtg atg gct ctc gtc gcc gtg ttt gtt gcc      219
Arg Arg Trp Leu Trp Leu Val Met Ala Leu Val Ala Val Phe Val Ala
 15                  20                  25 atg gtc atg tct tcc aga acc tct cca aaa nct ctg ttt gga gcc att      267
Met Val Met Ser Ser Arg Thr Ser Pro Lys Xaa Leu Phe Gly Ala Ile
 30                  35                  40                  45 gat aga gct tgt ccg tgt gct cgg ggc aca ccg aag tac agt ggc ann      315
Asp Arg Ala Cys Pro Cys Ala Arg Gly Thr Pro Lys Tyr Ser Gly Xaa
                 50                  55                  60 gtg gaa gat tgt tgt tgt gat tat gag anc gtg gat ngt tta atg aag      363
Val Glu Asp Cys Cys Cys Asp Tyr Glu Xaa Val Asp Xaa Leu Met Lys
                 65                  70                  75 aag tgt tgc aac ccn tnc ctc cag gan ctc gtg aaa gac ccc ttt ntt      411
Lys Cys Cys Asn Xaa Xaa Leu Gln Xaa Leu Val Lys Asp Pro Phe Xaa
 80                  85                  90 tcg ata ttt taa ngt gaa agt tat ggt ga                               440
Ser Ile Phe  *  Xaa Glu Ser Tyr Gly
 95                 100
```

<210> SEQ ID NO 8
<211> LENGTH: 101
<212> TYPE: PRT
<213> ORGANISM: Glycine max
<220> FEATURE:
<221> NAME/KEY: VARIANT
<222> LOCATION: (1)...(101)
<223> OTHER INFORMATION: Xaa = Any Amino Acid

<400> SEQUENCE: 8

```
Met Val Lys Ala Glu Ile Glu Lys Lys Gly Cys Ser Thr Arg Arg Trp
 1               5                  10                  15

Leu Trp Leu Val Met Ala Leu Val Ala Val Phe Val Ala Met Val Met
                 20                  25                  30

Ser Ser Arg Thr Ser Pro Lys Xaa Leu Phe Gly Ala Ile Asp Arg Ala
         35                  40                  45

Cys Pro Cys Ala Arg Gly Thr Pro Lys Tyr Ser Gly Xaa Val Glu Asp
 50                  55                  60

Cys Cys Cys Asp Tyr Glu Xaa Val Asp Xaa Leu Met Lys Lys Cys Cys
 65                  70                  75                  80

Asn Xaa Xaa Leu Gln Xaa Leu Val Lys Asp Pro Phe Xaa Ser Ile Phe
                 85                  90                  95

Xaa Glu Ser Tyr Gly
            100
```

<210> SEQ ID NO 9
<211> LENGTH: 1266
<212> TYPE: DNA
<213> ORGANISM: Triticum aestivum
<220> FEATURE:
<221> NAME/KEY: CDS
<222> LOCATION: (1)...(1264)

<400> SEQUENCE: 9

| | | | | | | | | | | | | | | | | |
|---|---|---|---|---|---|---|---|---|---|---|---|---|---|---|---|---|
| gga | ggc | tgc | ggc | tgc | ccc | ggc | gcg | agg | aag | tac | acg | ggg | atg | gtg | gag | 48 |
| Gly | Gly | Cys | Gly | Cys | Pro | Gly | Ala | Arg | Lys | Tyr | Thr | Gly | Met | Val | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | tgc | tgc | tgc | gac | tac | gag | acg | gtg | gac | gcc | atc | aac | gag | gag | gtg | 96 |
| Asp | Cys | Cys | Cys | Asp | Tyr | Glu | Thr | Val | Asp | Ala | Ile | Asn | Glu | Glu | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ctc | aac | ccg | atc | ctg | cag | gac | ctc | gtc | gct | ctg | ccc | ttc | ttc | agg | tac | 144 |
| Leu | Asn | Pro | Ile | Leu | Gln | Asp | Leu | Val | Ala | Leu | Pro | Phe | Phe | Arg | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| ttc | aag | gtt | aag | ttg | tgg | tgt | gac | tgc | cct | ttt | tgg | cct | gat | gat | ggc | 192 |
| Phe | Lys | Val | Lys | Leu | Trp | Cys | Asp | Cys | Pro | Phe | Trp | Pro | Asp | Asp | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| atg | tgt | cgg | ctc | agg | gac | tgt | agt | gta | tgc | gag | tgc | cca | gat | aat | gaa | 240 |
| Met | Cys | Arg | Leu | Arg | Asp | Cys | Ser | Val | Cys | Glu | Cys | Pro | Asp | Asn | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttt | ccc | gaa | cca | ttc | aag | aag | cct | tac | agt | ggc | ctt | tct | cct | gaa | aac | 288 |
| Phe | Pro | Glu | Pro | Phe | Lys | Lys | Pro | Tyr | Ser | Gly | Leu | Ser | Pro | Glu | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | atc | tgt | caa | gaa | gga | aaa | cca | gaa | gcc | act | gtt | gat | aga | acc | ctt | 336 |
| Met | Ile | Cys | Gln | Glu | Gly | Lys | Pro | Glu | Ala | Thr | Val | Asp | Arg | Thr | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gac | acc | aag | gtt | ttc | aaa | ggg | tgg | gtt | gaa | acc | gat | aat | cca | tgg | aca | 384 |
| Asp | Thr | Lys | Val | Phe | Lys | Gly | Trp | Val | Glu | Thr | Asp | Asn | Pro | Trp | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| tca | gat | gat | gag | acg | gat | aat | gct | gag | atg | act | tat | gtg | aat | ctt | caa | 432 |
| Ser | Asp | Asp | Glu | Thr | Asp | Asn | Ala | Glu | Met | Thr | Tyr | Val | Asn | Leu | Gln | |
| 130 | | | | | 135 | | | | | 140 | | | | | | |

| | | | | | | | | | | | | | | | | |
|---|---|---|---|---|---|---|---|---|---|---|---|---|---|---|---|---|
| ctt | aat | cct | gaa | cgt | tat | act | ggt | tat | act | ggt | gat | tca | gct | aga | agg | 480 |
| Leu | Asn | Pro | Glu | Arg | Tyr | Thr | Gly | Tyr | Thr | Gly | Asp | Ser | Ala | Arg | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ata | tgg | gac | gct | atc | tac | aaa | gaa | aat | tgc | cca | aaa | tat | cct | tca | gaa | 528 |
| Ile | Trp | Asp | Ala | Ile | Tyr | Lys | Glu | Asn | Cys | Pro | Lys | Tyr | Pro | Ser | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| gat | atg | tgc | cag | gag | aag | aag | gca | ctt | tac | aag | cta | att | tca | gga | ttg | 576 |
| Asp | Met | Cys | Gln | Glu | Lys | Lys | Ala | Leu | Tyr | Lys | Leu | Ile | Ser | Gly | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| cac | tcc | tca | ata | tct | gta | cat | att | gct | tat | gat | tat | ctt | ctt | gat | gaa | 624 |
| His | Ser | Ser | Ile | Ser | Val | His | Ile | Ala | Tyr | Asp | Tyr | Leu | Leu | Asp | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| tct | gct | aac | ttg | tgg | gga | cat | aat | ctt | ccg | ttg | ttg | cat | gac | cgt | gtt | 672 |
| Ser | Ala | Asn | Leu | Trp | Gly | His | Asn | Leu | Pro | Leu | Leu | His | Asp | Arg | Val | |
| | | | 210 | | | | | 215 | | | | | 220 | | | |

| | | | | | | | | | | | | | | | | |
|---|---|---|---|---|---|---|---|---|---|---|---|---|---|---|---|---|
| ctg | aag | tac | cca | gag | cgt | gtc | caa | aat | ctg | tac | ttc | aca | tac | cta | ttt | 720 |
| Leu | Lys | Tyr | Pro | Glu | Arg | Val | Gln | Asn | Leu | Tyr | Phe | Thr | Tyr | Leu | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtt | ctt | cgg | gca | gtg | act | aag | gcg | gca | gat | tac | ctt | gag | cag | gca | gag | 768 |
| Val | Leu | Arg | Ala | Val | Thr | Lys | Ala | Ala | Asp | Tyr | Leu | Glu | Gln | Ala | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| tac | aac | act | ggc | aat | cct | gaa | gag | gac | ttg | aaa | aca | caa | tct | tta | gtg | 816 |
| Tyr | Asn | Thr | Gly | Asn | Pro | Glu | Glu | Asp | Leu | Lys | Thr | Gln | Ser | Leu | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| agg | caa | ttg | ctt | tac | aac | cac | aag | tta | aga | tct | gca | tgt | cca | tta | cct | 864 |
| Arg | Gln | Leu | Leu | Tyr | Asn | His | Lys | Leu | Arg | Ser | Ala | Cys | Pro | Leu | Pro | |
| | | 275 | | | | | 280 | | | | | 285 | | | | |

| | | | | | | | | | | | | | | | | |
|---|---|---|---|---|---|---|---|---|---|---|---|---|---|---|---|---|
| ttt | gat | gaa | gca | aaa | ctc | tgg | caa | ggt | gaa | aat | ggc | cct | gag | tta | aag | 912 |
| Phe | Asp | Glu | Ala | Lys | Leu | Trp | Gln | Gly | Glu | Asn | Gly | Pro | Glu | Leu | Lys | |
| | | | 290 | | | | | 295 | | | | | 300 | | | |

-continued

```
cag gag att cag aag cag ttt aga aat att agt gca att atg gac tgt      960
Gln Glu Ile Gln Lys Gln Phe Arg Asn Ile Ser Ala Ile Met Asp Cys
305                 310                 315                 320 gtt ggt tgt gag aag tgt cga tta tgg gga aag ctt caa gtt ctt ggg     1008
Val Gly Cys Glu Lys Cys Arg Leu Trp Gly Lys Leu Gln Val Leu Gly
                325                 330                 335 ctt gga aca gca ctg aag att ctt ttt tct gtt gat gga gag aac aat    1056
Leu Gly Thr Ala Leu Lys Ile Leu Phe Ser Val Asp Gly Glu Asn Asn
            340                 345                 350 ttg aat cac aca ttc cag ctg cag cga aat gag gtc att gca ctg gta    1104
Leu Asn His Thr Phe Gln Leu Gln Arg Asn Glu Val Ile Ala Leu Val
        355                 360                 365 aat ctt ctg aat agg ctg tca gaa tct gtc aaa ttt gta cat gaa aca    1152
Asn Leu Leu Asn Arg Leu Ser Glu Ser Val Lys Phe Val His Glu Thr
370                 375                 380 gga tct tcc agc caa gaa gcc att aaa caa cag act ttc cac ttg gca    1200
Gly Ser Ser Ser Gln Glu Ala Ile Lys Gln Gln Thr Phe His Leu Ala
385                 390                 395                 400 aaa gag ggc ttc ctg acc aaa tgt gaa acg tat cct gca aag ata caa    1248
Lys Glu Gly Phe Leu Thr Lys Cys Glu Thr Tyr Pro Ala Lys Ile Gln
                405                 410                 415 gag agc aat ttg ttt t ga                                            1266
Glu Ser Asn Leu Phe
            420
```

<210> SEQ ID NO 10
<211> LENGTH: 421
<212> TYPE: PRT
<213> ORGANISM: Triticum aestivum

<400> SEQUENCE: 10

```
Gly Gly Cys Gly Cys Pro Gly Ala Arg Lys Tyr Thr Gly Met Val Glu
1               5                   10                  15

Asp Cys Cys Asp Tyr Glu Thr Val Asp Ala Ile Asn Glu Glu Val
            20                  25                  30

Leu Asn Pro Ile Leu Gln Asp Leu Val Ala Leu Pro Phe Phe Arg Tyr
        35                  40                  45

Phe Lys Val Lys Leu Trp Cys Asp Cys Pro Phe Trp Pro Asp Asp Gly
    50                  55                  60

Met Cys Arg Leu Arg Asp Cys Ser Val Cys Glu Cys Pro Asp Asn Glu
65                  70                  75                  80

Phe Pro Glu Pro Phe Lys Lys Pro Tyr Ser Gly Leu Ser Pro Glu Asn
                85                  90                  95

Met Ile Cys Gln Glu Gly Lys Pro Glu Ala Thr Val Asp Arg Thr Leu
            100                 105                 110

Asp Thr Lys Val Phe Lys Gly Trp Val Glu Thr Asp Asn Pro Trp Thr
        115                 120                 125

Ser Asp Asp Glu Thr Asp Asn Ala Glu Met Thr Tyr Val Asn Leu Gln
    130                 135                 140

Leu Asn Pro Glu Arg Tyr Thr Gly Tyr Thr Gly Asp Ser Ala Arg Arg
145                 150                 155                 160

Ile Trp Asp Ala Ile Tyr Lys Glu Asn Cys Pro Lys Tyr Pro Ser Glu
                165                 170                 175

Asp Met Cys Gln Glu Lys Lys Ala Leu Tyr Lys Leu Ile Ser Gly Leu
            180                 185                 190

His Ser Ser Ile Ser Val His Ile Ala Tyr Asp Tyr Leu Leu Asp Glu
        195                 200                 205
```

```
-continued

Ser Ala Asn Leu Trp Gly His Asn Leu Pro Leu Leu His Asp Arg Val
    210                 215                 220

Leu Lys Tyr Pro Glu Arg Val Gln Asn Leu Tyr Phe Thr Tyr Leu Phe
225                 230                 235                 240

Val Leu Arg Ala Val Thr Lys Ala Ala Asp Tyr Leu Glu Gln Ala Glu
                245                 250                 255

Tyr Asn Thr Gly Asn Pro Glu Glu Asp Leu Lys Thr Gln Ser Leu Val
                260                 265                 270

Arg Gln Leu Leu Tyr Asn His Lys Leu Arg Ser Ala Cys Pro Leu Pro
                275                 280                 285

Phe Asp Glu Ala Lys Leu Trp Gln Gly Glu Asn Gly Pro Glu Leu Lys
    290                 295                 300

Gln Glu Ile Gln Lys Gln Phe Arg Asn Ile Ser Ala Ile Met Asp Cys
305                 310                 315                 320

Val Gly Cys Glu Lys Cys Arg Leu Trp Gly Lys Leu Gln Val Leu Gly
                325                 330                 335

Leu Gly Thr Ala Leu Lys Ile Leu Phe Ser Val Asp Gly Glu Asn Asn
                340                 345                 350

Leu Asn His Thr Phe Gln Leu Gln Arg Asn Glu Val Ile Ala Leu Val
            355                 360                 365

Asn Leu Leu Asn Arg Leu Ser Glu Ser Val Lys Phe Val His Glu Thr
370                 375                 380

Gly Ser Ser Ser Gln Glu Ala Ile Lys Gln Gln Thr Phe His Leu Ala
385                 390                 395                 400

Lys Glu Gly Phe Leu Thr Lys Cys Glu Thr Tyr Pro Ala Lys Ile Gln
                405                 410                 415

Glu Ser Asn Leu Phe
            420

<210> SEQ ID NO 11
<211> LENGTH: 36
<212> TYPE: DNA
<213> ORGANISM: Artificial Sequence
<220> FEATURE:
<223> OTHER INFORMATION: Sal-A20 oligonucleotide

<400> SEQUENCE: 11
tcgacccacg cgtccgaaaa aaaaaaaaaa aaaaaa                                36
```

NUCLEIC ACID ENCODING MAIZE ENDOPLASMIC RETICULUM OXIDOREDUCTIN AND METHOD OF USE

CROSS-REFERENCE TO RELATED APPLICATION

This application claims priority to and the benefit of U.S. Provisional Application No. 60/284,481 filed Apr. 18, 2001.

FIELD OF THE INVENTION

The invention relates to plant metabolism, particularly to genes encoding endoplasmic reticulum oxidoreductin and to the alteration of such genes in plants.

BACKGROUND OF THE INVENTION

A major focus of crop plant breeders over the last fifty years has been the modification of traits that affect seed composition. Of particular interest to plant breeders have been traits that affect the energy reserves of the seed, including protein and starch. The efforts of plant breeders have led to the development and introduction of crop plants with modified levels and characteristics of these traits.

While mankind has derived many benefits from the past efforts of plant breeders, the combination of the rapidly increasing human population and the decline in land available for agriculture places a tremendous burden on agriculturists to increase both agricultural output and productivity. New and improved crop plant varieties are desired by agriculturists to help meet the challenge of feeding the world's human population. Although traditional plant breeding approaches for crop plant improvement have been successful, the traditional approaches are slow and limited to naturally occurring genetic variation or artificially induced mutations. To keep pace with the escalating demands that the increase in the world's population places on agriculture, more rapid approaches for developing crop plants are necessary. The recombinant-DNA-based methodologies of genetic engineering have already been used successfully to incorporate new insect-resistance and herbicide-tolerance traits into crop plants. Such methodologies have great potential for modifying other characteristics of crop plants including the starch and protein in seeds.

SUMMARY OF THE INVENTION

Methods and compositions are provided for altering the synthesis of endoplasmic reticulum oxidoreductin protein in plants. Endoplasmic reticulum oxidoreductin plays an important role in regulating the oxidative conditions in the endoplasmic reticulum.

Endoplasmic reticulum oxidoreductin contains a conserved motif of $C^{391}$ X X $C^{394}$ X(acidic) X(basic) $C^{397}$. (Numbering based upon human ERO-1 sequence, accession no. AF081886). The CXXC motif is similar to the motif found on most oxidoreductases, such as thioredoxin and protein disulfide isomerase. The $NH^2$ region among endoplasmic reticulum oxidoreductase genes from different species is highly variable, with the common feature among these variable regions being hydrophobicity. (Cabibbo et al. 2000). Endoplasmic reticulum oxidoreductin contains a signal peptide that is likely not cleaved, and this uncleaved signal peptide may function as a transmembrane domain.

Compositions provided herein comprise nucleotide sequences encoding plant endoplasmic reticulum oxidoreductins. The nucleotide sequences of the invention are useful in transforming plants for tissue-preferred, seed-preferred, and constitutive expression of endoplasmic reticulum oxidoreductin. The compositions find use in methods for altering disulfide bond formation of proteins in plant cells, particularly proteins folded in the lumen of the endoplasmic reticulum. The methods involve altering endoplasmic reticulum oxidoreductin activity to change disulfide bond formation in either native or transgenic plant proteins.

Alteration in native proteins, via a change in the oxidative environment of the endoplasmic reticulum, is useful for changing the characteristics of the seed starch-protein matrix. In many seeds, seed storage proteins account for 50% or more of the total protein. In cereals, the endosperm is generally the major seed tissue, and the ethanol-soluble fraction of the grain endosperm proteins in corn are referred to as prolamins. In the case of corn, the endosperm accounts for 80% of the corn kernel, and approximately 80% of corn endosperm proteins are prolamins known as zeins. Corn endosperm consists of a dense matrix of starch granules and protein bodies (the starch-protein matrix) and, as mentioned above, approximately 80% of corn endosperm proteins are zeins. The biogenesis and composition of the endosperm matrix determine to a large part the physical properties of the grain (e.g., starchy, horny, opaque or vitreous endosperm). The protein bodies of the corn endosperm are assembled in the endoplasmic reticulum. During this process the zein proteins are synthesized by membrane-bound polyribosomes and are co-translationally translocated into the lumen of where they are assembled into protein bodies. Zein proteins interact during formation of protein bodies, and these interactions are important for the formation of proteolytically stable complexes. The gamma-zeins are disulfide-rich proteins. Beta-zein is a hydrophobic, methionine-rich 15 kD protein. The gamma-zeins and beta-zein form intermolecular disulfide bridges and hydrophobic interactions, and are located near the periphery of protein bodies. Additional proteins that are sequestered into the protein bodies include alpha-zeins, delta-zeins, and matrix proteins. Thus, altering the starch-protein matrix will produce grain with starch characteristics exhibiting improved nutritional value for food and feed and improved processing qualities.

As taught by Applicant herein, this alteration may be accomplished through reducing oxidative conditions in the endoplasmic reticulum and thereby decreasing the amount of cross linking in seed proteins such as prolamins. Such decreased cross linking will cause more extractable starch and more digestible grain to be produced. This is because the presence of these protein bodies in seed, such as corn, interferes with the release of starch granules in the corn wet-milling process. Current industry practices involve maximizing the release of intact starch granules in the corn wet-milling process by steeping the corn with large amounts of sulfur-reducing chemicals (e.g., sodium bisulfite). This process is time intensive and is environmentally insensitive as it produces substantial amounts of waste material. By altering the amount of disulfide cross linking in prolamins with a high disulfide content, such as gamma-zein, the amount of sulfur-reducing chemicals needed may be decreased or possibly even eliminated. This may be accomplished through Applicant's invention as described herein.

In addition to altering starch-protein matrix characteristics of seeds, functional properties, such as rheological and gelation properties will also be altered, which will be particularly useful in crops, such as soybean, that have a large amount of protein in the seed. The rheological and gelation properties of proteins are greatly affected by the cross-linking within proteins and between proteins. By affecting the oxidative conditions of the endoplasmic reticulum, the amount of protein cross-linking is affected, and this alters seed rheological and gelation properties.

Applicant also teaches that the import into the endoplasmic reticulum of transgenic polypeptides bearing multiple disulfide-bridge forming cysteines leads to reduced oxidative conditions in the endoplasmic reticulum. This results in an unfolded protein response by the cell in which improperly folded proteins are degraded, which reduces the accumulation of the transgenic polypeptides. Applicant teaches utilizing endoplasmic reticulum oxidoreductin to correct this problem by increasing the oxidative conditions in the endoplasmic reticulum.

Expression cassettes comprising endoplasmic reticulum oxidoreductin nucleotide sequences of the invention are provided. Additionally provided are transformed plants, plant tissues, plant cells, and seeds thereof. Isolated proteins encoded by the nucleotide sequences of the invention are also provided.

BRIEF DESCRIPTION OF THE DRAWINGS

FIG. 1 is a trace modulation of fragment 186.8 in comparison of W64A vs. W64A-fl2. W64A (wild type) is shown in the top graph. W64A-fl2 (mutant) is shown in the bottom graph.

FIG. 2 is a confirmation by competitive PCR of the fragment 186.8 as an ERO gene. W64A (wild type) is shown in the top graph. W64A-fl2 (mutant) is shown in the bottom graph.

FIG. 3 is a trace modulation of fragment 301.4 in comparison of W64A vs W64A-Mc. W64A (wild type) is shown in the top graph. W64A-Mc mutant is shown in the bottom graph.

FIG. 4 is a confirmation by competitive PCR of the fragment 301.4 as an ERO1 gene. W64A (wild type) is shown in the top graph. W64A-Mc mutant is shown in the bottom graph.

DETAILED DESCRIPTION OF THE INVENTION

The present invention is drawn to compositions and methods for improving plants. The invention provides compositions and methods that find use in altering the oxidative conditions in the endoplasmic reticulum of plant cells. The methods find further use in modifying the protein and starch-protein matrix characteristics of plant tissues, particularly seed starch-protein matrices. The methods also find use in alleviating the unfolded protein response often caused by the introduction of a transgenic protein. The compositions comprise isolated plant nucleotide sequences encoding endoplasmic reticulum oxidoreductin and the isolated proteins encoded by such nucleotide sequences.

The invention provides plants, plant tissues, plant cells, and seeds thereof that are genetically modified to alter the synthesis of endoplasmic reticulum oxidoreductin therein. Plants possessing the desired alteration in endoplasmic reticulum oxidoreductin can be selected by measuring the level of RNA or protein produced in the plant, or in one or more parts thereof including, but not limited to, seeds, fruits, leaves, stems, roots, flowers, embryos, cotyledons, endosperm, and scutellum. Such plant may also be selected by measuring the phenotypic or molecular differences caused by the altered oxidative conditions in the endoplasmic reticulum of the altered plant or plant part. These differences can be measured by methods known in the art including, but not limited to, NMR, HPLC, GC, GC-MS, TLC, immunoassays, and the like. If necessary, the desired components or molecules can be extracted from plant tissues using standard extraction techniques that are known in the art.

Compositions of the invention include nucleotide sequences encoding endoplasmic reticulum oxidoreductin. In particular, the present invention provides for isolated nucleic acid molecules comprising nucleotide sequences encoding the amino acid sequences shown in SEQ ID NOs: 2, 4, 6, 8 or 10. Further provided are polypeptides having an amino acid sequence encoded by a nucleic acid molecule described herein, for example those set forth in SEQ ID NOs: 1, 3, 5, 7 or 9, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence endoplasmic reticulum oxidoreductin activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of an endoplasmic reticulum oxidoreductin nucleotide sequence that encodes a biologically active portion of an endoplasmic reticulum oxidoreductin of the invention will encode at least 15, 25, 30, 50, 100, 150, 200, 250, 350, 400, 450, 500 or 550 contiguous amino acids, or up to the total number of amino acids present in a full-length endoplasmic reticulum oxidoreductin of the invention (for example, amino acids for SEQ ID NOs: 2, 4, 6, 8 and 10, respectively). Fragments of an endoplasmic reticulum oxidoreductin nucleotide sequence that are useful as hybridization probes or PCR primers generally need not encode a biologically active portion of an endoplasmic reticulum oxidoreductin.

Thus, a fragment of an endoplasmic reticulum oxidoreductin sequence may encode a biologically active portion of an endoplasmic reticulum oxidoreductin, or it may be a fragment that can be used as a hybridization probe or PCR primer using methods disclosed below. A biologically active portion of an endoplasmic reticulum oxidoreductin can be prepared by isolating a portion of one of the endoplasmic reticulum oxidoreductin nucleotide sequences of the invention, expressing the encoded portion of the endoplasmic reticulum oxidoreductin (e.g., by recombinant expression in vitro), and assessing the activity of the encoded portion of the endoplasmic reticulum oxidoreductin. Nucleic acid molecules that are fragments of an endoplasmic reticulum oxidoreductin nucleotide sequence comprise at least 16, 20, 30, 40, 50, 60, 75, 100, 150, 200, 250, 300, 350, 400, 450, 500, 550, 600, 650, 700, 800, 900, 1,000, 1,100, 1,200, 1,300, 1,400, 1,500, 1,600 or up to the number of nucleotides present in a full-length endoplasmic reticulum oxidoreductin nucleotide sequence disclosed herein (for example, nucleotides for SEQ ID NOs: 1, 3, 5, 7 and 9, respectively).

By "variants" is intended substantially similar sequences. For nucleotide sequences, conservative variants include those sequences that, because of the degeneracy of the genetic code, encode the amino acid sequence of one of the endoplasmic reticulum oxidoreductin polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode an endoplasmic reticulum oxidoreductin protein of the invention. Generally, variants of a particular nucleotide sequence of the invention will have at least about 65%, 70%, generally at least about 75%, 80%, 85%, preferably at least about 86%, 87%, 88%, 89%, 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or the addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, endoplasmic reticulum oxidoreductin activity as described herein. Such variants may result from, for example, genetic polymorphism or from human manipulation. Biologically active variants of a native endoplasmic reticulum oxidoreductin of the invention will have at least about 75%, 80%, generally at least about, 81%, 82, 83%, preferably at least about 84%, 85%, 86%, 87%, 88%, 89%, 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue. The proteins of the invention may be altered in various ways including amino acid substitutions, deletions, truncations, and insertions. Methods for such manipulations are generally known in the art. For example, amino acid sequence variants of the endoplasmic reticulum oxidoreductins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as variations and modified forms thereof. Likewise, the proteins of the invention encompass both naturally occurring proteins as well as variations and modified forms thereof. Such variants will continue to possess the desired endoplasmic reticulum oxidoreductin activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by phenotypic changes or by endoplasmic reticulum oxidoreductin activity assays. See, for example, Coughlan, et. al., (1996), Molecular Characterization of Plant Endoplasmic Reticulum, Identification of Protein Disulfide Isomerase as the Major Reticuloplasmin., Eur. J. Biochem., 235:215–224 and Methods of Enzymatic Analysis, Vol. 1 ((1974). Bergmeyer, ed., Verlag Chemie, Weinheim), herein incorporated by reference.

Variant nucleotide sequences and proteins also encompass sequences and proteins derived from a mutagenic and recombinogenic procedure such as DNA shuffling. With such a procedure, one or more different endoplasmic reticulum oxidoreductin coding sequences can be manipulated to create a new endoplasmic reticulum oxidoreductin possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between one or more endoplasmic reticulum oxidoreductin genes of the invention and other known endoplasmic reticulum oxidoreductin genes to obtain a new gene coding for a protein with an improved property of interest, such as an increased $K_m$ in the case of an enzyme. Alternatively, two or more of the endoplasmic reticulum oxidoreductin genes of the invention may be shuffled together. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire endoplasmic reticulum oxidoreductin nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the endoplasmic reticulum oxidoreductin sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire endoplasmic reticulum oxidoreductin nucleotide sequence disclosed herein, or one or more portions thereof, may be used as a probe capable of specifically hybridizing to corresponding endoplasmic reticulum oxidoreductin nucleotide sequences and messenger RNAs. To achieve specific hybridization under a variety of conditions, such probes include sequences that are unique among endoplasmic reticulum oxidoreductin nucleotide sequences and are preferably at least about 10 nucleotides in length, and most preferably at least about 20 nucleotides in length. Such probes may be used to amplify corresponding endoplasmic reticulum oxidoreductin nucleotide sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will selectively hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)− 500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$)

for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode an endoplasmic reticulum oxidoreductin and which selectively hybridize under stringent conditions to the endoplasmic reticulum oxidoreductin nucleotide sequences disclosed herein, or to fragments thereof, are encompassed by the present invention. Such sequences will be at least about 65% to 70% homologous, about 75%, or 80% homologous, and even at least about 85%, 86%, 87%, 88%, 89%, 90%, 91%, 92%, 93%, 94%, 95%, 96%, 97%, 98%, 99% or more homologous with the disclosed sequences. That is, the sequence identity of sequences may range, sharing at least about 65% to 70%, about 75%, or 80%, and even at least about 85%, 86%, 87%, 88%, 89%, 90%, 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, the full length of the coding region (the sequence from the start codon to the stop codon) of a cDNA or gene sequence, or the complete cDNA or gene sequence including the 5' and/or 3' un-translated region.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.hlm.nih.gov. Unless specified herein, references to BLAST made herein refer to BLAST2.0, NCBI-BLAST version, and its corresponding filtering, default parameters, two-hit algorithm and statistics, as versus the BLAST2.0, WU-BLAST version, and its corresponding filtering, default parameters, two-hit algorithm and statistics. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Windows of comparison that may be used are the full length of a sequence, for example, Seq. Ids. No. 1, 3, 5, 7 or 9, or alternatively, the full length of the coding region of a sequence, such as the coding region of Seq. Ids. No. 1, 3, 5, 7 or 9. In such cases, the percentage of sequence identity refers to the global alignment between the two sequences, as versus the local alignments that may occur within subsections of the comparison window.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The endoplasmic reticulum oxidoreductins nucleotide sequences of the invention are, in some embodiments, characterized as "intronless" nucleotide sequences. These are nucleotide sequences that, as distinguished from most genomic sequences, do not contain introns. Such introns may be removed by any method known in the art, including by the creation of a cDNA of a particular genomic sequence.

The endoplasmic reticulum oxidoreductin nucleotide sequences of the invention are provided in expression cassettes for expression in the plant of interest. The cassette will include 5' and 3' regulatory sequences operably linked to an endoplasmic reticulum oxidoreductin sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the endoplasmic reticulum oxidoreductin nucleotide sequence to be under the transcriptional regulation of the regulatory regions. The expression cassette may additionally contain selectable marker genes.

The expression cassette will include in the 5'-3' direction of transcription, a transcriptional and translational initiation region, an endoplasmic reticulum oxidoreductin DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence. That is the transcription initiation region is any transcription initiation region except the native, unmodified transcription initiation region of that coding region.

While it may be preferable to express the sequences using heterologous promoters, the native promoter sequences may be used. Such constructs would change expression levels of endoplasmic reticulum oxidoreductin in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol* 92: 1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991)

*Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced endoplasmic reticulum oxidoreductin expression within a particular plant tissue. Tissue-preferred promoters include Yamamoto et al. (1997) *Plant J* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505. All of such promoters can be modified, if necessary, for weak expression.

Leaf-preferred promoters are known in the art. See, for example, Yamamoto et al. (1997) *Plant J.* 12(2):255–265; Kwon et al. (1994) *Plant Physiol.* 105:357–67; Yamamoto et al. (1994) *Plant Cell Physiol.* 35(5):773–778; Gotor et al. (1993) *Plant J.* 3:509–18; Orozco et al. (1993) *Plant Mol. Biol.* 23(6):1129–1138; and Matsuoka et al. (1993) *Proc. Natl. Acad. Sci. USA* 90(20):9586–9590.

Root-preferred promoters are known and can be selected from the many available from the literature or isolated de novo from various compatible species. See, for example, Hire et al. (1992) *Plant Mol. Biol.* 20(2): 207–218 (soybean root-preferred glutamine synthetase gene); Keller and Baumgartner (1991) *Plant Cell* 3(10):1051–1061 (root-preferred control element in the GRP 1.8 gene of French bean); Sanger et al. (1990) *Plant Mol. Biol.* 14(3):433–443 (root-preferred promoter of the mannopine synthase (MAS) gene of *Agrobacterium tumefaciens*); and Miao et al. (1991) *Plant Cell* 3(1):11–22 (full-length cDNA clone encoding cytosolic glutamine synthetase (GS), which is expressed in roots and root nodules of soybean). See also Bogusz et al. (1990) *Plant Cell* 2(7):633–641, where two root-preferred promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-preferred promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69–76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343–350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4): 759–772); and rolB promoter (Capana et al. (1994) *Plant Mol. Biol.* 25(4):681–691. See also U.S. Pat. Nos. 5,837, 876; 5,750,386; 5,633,363; 5,459,252; 5,401,836; 5,110, 732; and 5,023,179. Tissue preferred and specific promoters also include the tissue specific and tissue preferred promoters listed in PCT application publication number WO 00/36124, Page 35, Table A, which table is hereby incorporated by reference.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see the copending application entitled "Seed-Preferred Promoters," U.S. Application Ser. No. 60/097,233, filed Aug. 20, 1998, herein incorporated by reference). Gama-zein is a preferred endosperm-preferred promoter. Glob-1 is a preferred embryo-preferred promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, γ-zein, waxy, shrunken-1, shrunken-2, globulin-1, etc. A seed endosperm specific promoter would be most preferred for use with the present invention.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell*

49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10: 143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology, Vol.* 78 (Springer-Verlag, Berlin); Gill et al. (1988) *Nature* 334: 721–724. Such disclosures are herein incorporated by reference.

The above list of selectable marker genes is not meant to be limiting. Any selectable marker gene can be used in the present invention.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

It is recognized that with these nucleotide sequences, antisense constructions, complementary to at least a portion of the messenger RNA (mRNA) for the endoplasmic reticulum oxidoreductin sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding sense sequences may be used.

The nucleotide sequences of the present invention may also be used in the sense orientation to suppress the expression of endogenous genes in plants. Methods for suppressing gene expression in plants using nucleotide sequences in the sense orientation are known in the art and are often referred to as co-suppression methods. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The invention additionally encompasses nucleotide sequences encoding variant polypeptides that can be used in dominant-negative strategies to reduce a particular biological activity within an organism or cell thereof. Such dominant-negative strategies are known in the art and can involve the expression of a modified subunit of a multisubunit protein. Generally, such a modified subunit comprises a polypeptide that is able to affect, or interact with, other members of the multisubunit protein complex and thereby reduce, or eliminate, the biological activity of the complex. It is recognized that such dominant-negative strategies can be used to reduce or eliminate the activity of both homomeric enzymes and heteromeric enzymes. By "homomeric enzyme" is intended an enzyme that is comprised of two or more subunits each having the same amino acid sequences. By "heteromeric enzyme" is intended an enzyme that is comprised of two or more subunits wherein not all the subunits comprise the same amino acid sequence. While the methods of the invention do not depend on a particular biological mechanism, typically such a dominant-negative approach will involve the expression of a variant of a polypeptide of the invention that does not possess the complete biological activity of the native polypeptide. It is recognized that such an dominant-negative approach does not depend on eliminating or reducing the expression of native genes in a plant, only that such an approach involves the expression of nucleotide sequence of the invention that encodes a variant polypeptide that is capable of causing a reduction or elimination of the desired biological activity in a plant or cell thereof.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Preferably, plants of the present invention are crop plants (for example, corn, soybean, *Brassica*, wheat, rice, sunflower, cotton, safflower, peanut, *sorghum*, alfalfa, millet, tobacco, etc.). Plants of particular interest include grain plants that provide seeds of interest, oilseed plants, and leguminous plants. Seeds of interest include grain seeds, such as corn, wheat, barley, rice, *sorghum*, rye, etc. Oilseed plants include soybean, *Brassica*, safflower, sunflower, cotton, maize, peanut, alfalfa, palm, sesame, coconut, etc. Leguminous plants include beans and peas. Beans include soybean, guar, locust bean, fenugreek, garden beans, cowpea, mungbean, lima bean, fava bean, lentils, chickpea, etc.

The invention involves the use of endoplasmic reticulum oxidoreductin to alter the oxidative conditions in the endoplasmic reticulum of a plant cell. This alteration of the oxidative conditions in the endoplasmic reticulum will alter the capability of the plant, plant part or plant cell, to properly accumulate polypeptides with disulfide bonds. These polypeptides with disulfide bonds may be native or transgenic, and the oxidative conditions in the endoplasmic reticulum may be either increased or decreased. When Applicants refer to a level of disulfide bonds herein, Applicants mean the portion of cysteine residues within a protein or between proteins that participate in disulfide bonds or disulfide bridges, and such portion may be expressed as a percentage.

To allow efficient disulfide folding the endoplasmic reticulum must maintain a particular re-dox potential. Under strongly reducing conditions, as in the cytosol of the cell, disulfide bonds formation is disfavored. Conversely, strongly oxidizing conditions will result in improper polypeptide folding because of the formation of incorrect disulfide bonds. Endoplasmic reticulum oxidoreductin polynucleotides may be utilized to regulate desired oxidative conditions in the endoplasmic reticulum of plant cells.

Until now, the effect of the up or down regulation of endoplasmic reticulum oxidoreductin in plant cells has not been known. Applicants have performed extensive characterization of plants mutated or transgenically modified to contain polypeptides bearing multiple disulfide-bridge forming cysteines (See Example 4). These plants contained seed with altered starch phenotypes, such as starchy, horny, opaque or vitreous endosperm and contained seed with altered rheological and gelation properties. Many of these mutated or transgenically modified plants also did not properly accumulate protein because of a shortage of oxidative equivalents in the endoplasmic reticulum. As a result, polypeptide chains could not achieve their proper secondary and tertiary structure, and an unfolded protein response was induced that involved the degradation of the improperly folded polypeptides and affected plant phenotype. Over expression of endoplasmic reticulum oxidoreductin in plants or plant cells counteracts this type of induced unfolded protein response. This enables the proper accumulation of polypeptides in transgenically modified plants. This aspect of the invention has particular use in protein farming of polypeptides of biotechnological or pharmaceutical interest. The altered expression of endoplasmic reticulum oxidoreductin in plants or plant cells may be accomplished by the methods described above. In one embodiment of this aspect of the invention, a seed specific promoter, such as 27 kD gamma zein promoter, a corn globulin 1 promoter or a phaseolin promoter may be used, thereby allowing the accumulation of the endoplasmic reticulum oxidoreductin protein in the seed. An additional benefit of this aspect of the invention may also be reduced allergenicity and inactivation of proteinase and amylase inhibitors in protein for feed and food use.

Altering the oxidative conditions in the endoplasmic reticulum of a plant cell can have profound effects on other metabolic processes in the cell, particularly on the proteins and carbohydrates that accumulate in the cell. Disulfide bond formation has a significant impact on the starch-protein matrix characteristics of the cell, particularly a seed cell, which will range in waxy, starchy, horny, opaque or vitreous endosperm characteristics. Alterations in the oxidative conditions of the endoplasmic reticulum cause corresponding changes to the starch-protein matrix characteristics by altering the amount of disulfide crosslinking within and between seed storage proteins with a large number of disulfide bonds. This may be particularly useful for affecting the cross linking of seed storage proteins, especially the prolamins, and in particular the zeins, which have a profound affect on the seed starch-protein matrix characteristics. The invention is particularly useful in the inducement of corn with a vitreous kernel phenotype, which phenotype is characterized by a corn endosperm of normal testweight that is translucent when viewed through a bright light source.

The opaque phenotype is observed when endoplasmic reticulum oxidoreductin activity is either greater than or less than the wild type level of endoplasmic reticulum oxidoreductin activity. The vitreous phenotype is observed when endoplasmic reticulum oxidoreductin activity is within normal levels. The present invention may be used to bring endoplasmic oxidoreductin activity to within normal levels. Normal levels will vary with the intended use of the grain, but may be within either plus or minus 1.1X, 1.2X, 1.3X, 1.4X, 1.5X, 2.0X, 2.5X, 5X, 10X, 15X, 20X, 25X, 30X, 40X or 50X, where X is the wild type level of endoplasmic reticulum oxidoreductin activity. For example, when insertion of a transgene of interest correlates with a movement of endoplasmic reticulum oxidoreductin activity to a range outside of normal levels, the present invention may be utilized to bring endoplasmic reticulum oxidoreductin activity within those normal levels, thereby obtaining a more vitreous grain phenotype.

The intermolecular disulfide bridges of the gamma-zeins, along with the hydrophobic beta-zein, and alpha- and delta-zeins, are important for the formation and maintenance of protein bodies. These protein bodies contribute to the physical properties of the grain. Zein proteins interact during formation of protein bodies (through intermolecular disulfide bonds and hydropobic inteactions), and these interactions are important for the formation of proteolytically stable complexes. While the methods of the present invention do not depend on any particular biological mechanism, it is recognized that because of its role in the formation of disulfide bonds between proteins, an alteration in endoplasmic reticulum oxidoreductin activity can reasonably be expected to have an effect on the formation of protein bodies. This will resulting in a corresponding alteration in grain digestibility in grain used for human or animal feed and in the release of starch granules in grain used in the wet-milling properties. An improvement in digestibility and wet-milling properties is especially beneficial for plants with high seed starch content such as corn and *sorghum*.

An enzyme digestible dry matter (EDDM) assay used as an indicator of in vivo digestibility is known in the art and can be performed according to the methods described in Boisen and Fernandez (1997) *Animal Feed Science and Technology* 68:83–92, and Boisen and Fernandez (1995) *Animal Feed Science and Technology* 51:29–43; which are herein incorporated in their entirety by reference.

Although seed with extensive disulfide bonding exhibits poor wet-milling properties and decreased dry matter digestibility, a high disulfide-status has also been correlated with increased seed hardness and improved dry-milling properties. In fact, the transcript level of endoplasmic reticulum oxidoreductin has been shown to be largely affected in several opacity mutants (see Example 4) and in opaque high lysine corn. Assays for seed hardness are well known in the art and include such methods as those described in Pomeranz et al. (1985) *Cereal Chemistry* 62:108–112; herein incorporated in its entirety by reference. Assays to measure the testweight of grain are also well known in the art.

Many of the zein proteins, especially the gamma-zeins, have a high number of disulfide bonds and participate in intermolecular protein cross-linking. For this reason, maintaining proper oxidative conditions in the endoplasmic reticulum is important to increase seed hardness. The ability to confer seed hardness is particularly useful in the case of soft kernel phenotypes that are induced by mutation or transgenic polypeptides.

Methods are provided for altering the oxidative conditions of the endoplasmic reticulum of a plant cell. The methods find use in affecting starch-protein matrix characteristics, seed Theological and gelation properties, and reducing the unfolded protein response caused by the introduction of a transgenic polynucleotide, particularly a polynucleotide encoding a polypeptide that will form sufficient disulfide bonds to affect the oxidative conditions of the endoplasmic reticulum. In particular, the methods find use in the production of improved cultivars of crop plants with these benefits. The methods involve introducing into a plant a nucleotide construct comprising at least a portion of a nucleotide sequence encoding an endoplasmic reticulum oxidoreductin. The methods do not depend on a particular nucleotide sequence encoding an endoplasmic reticulum oxidoreductin, only that such an endoplasmic reticulum oxidoreductin nucleotide sequence is capable of significantly and beneficially affecting the oxidative conditions of the plant cell endoplasmic reticulum. Any nucleotide sequence that is known in the art that encodes an endoplasmic reticulum oxidoreductin sequence can be employed, although plant endoplasmic reticulum oxidoreductin nucleotide sequences are preferred. Such endoplasmic reticulum oxidoreductin nucleotide sequences are not limited to naturally occurring nucleotide sequences, but also include modified sequences. Preferred endoplasmic reticulum oxidoreductin nucleotide sequences are the sequences set forth in SEQ. ID Nos 1, 3, 5, 7 and 9. The *Arabidopsis thaliana* genomic sequence may be used, in addition to the coding region for an endoplasmic reticulum oxidoreductin shown as a computer predicted coding region for an unknown protein (see genbank accession numbers AC067754 and AC005770).

If increased expression of endoplasmic reticulum oxidoreductin is desired, the nucleotide construct will additionally comprise an operably linked promoter that drives expression in a plant cell. Preferred promoters are seed-preferred, constitutive, developmentally regulated, and chemical-regulated promoters.

If a decreased level or activity of endoplasmic reticulum oxidoreductin is desired, the methods of the invention can additionally comprise antisense suppression, co-suppression, and chimeraplasty. Such methods are known in the art. In antisense suppression methods, an endoplasmic reticulum oxidoreductin nucleotide sequence can be operably linked to a promoter that drives expression in a plant for the production of antisense transcripts. In co-suppression methods, an endoplasmic reticulum oxidoreductin nucleotide sequence can be operably linked to a promoter that drives expression in a plant for the production of sense transcripts. With chimeraplasty, no promoter is necessary; only an endoplasmic reticulum oxidoreductin nucleotide sequence, or portion thereof is used.

If desired, one or more additional nucleotide constructs may be introduced into the plant. Preferably, such nucleotide constructs comprise at least a portion of a nucleotide sequence of an enzyme, or other protein, that is capable of affecting the oxidative conditions of the endoplasmic reticulum. Such sequences would include those that code for protein disulfide isomerase (for example, corn pdi with genbank accession number L39014), endoplasmic reticulum glutathione reductase or thioredoxins (for example, see genbank accession numbers L40957, AJ404845 and X73549). Such nucleotide constructs also may comprise at least a portion of a nucleotide sequence of an enzyme, or other protein, that is capable of affecting the starch-protein matrix or protein characteristics of the plant cell. Such sequences would include those that code for prolamins, and especially zeins, and most especially gamma zeins (for example, see genbank accession numbers X55726, X05911, M16066, M16460, U25674, L29505 and M13507). If expression of the nucleotide sequence is desired, the nucleotide construct can additionally comprise an operably linked promoter.

In one embodiment of the invention, the methods of the invention provide a plant, particularly a maize plant, that produces seeds or kernels with increased starch hardness in the endosperm. The methods involve stably incorporating into the genome of a plant a nucleotide construct comprising an endoplasmic reticulum oxidoreductin nucleotide sequence operably linked to a promoter that drives expression in a developing seed. Preferably, the nucleotide sequence is the nucleotide sequence set forth in SEQ ID NO: 1, 3, 5, 7 or 9. Preferred promoters are promoters that direct expression preferentially in seeds including, but not limited, to the 27 kD gamma zein promoter, a corn globulin 1 promoter or a phaseolin promoter.

The following examples are presented by way of illustration, not by way of limitation.

EXPERIMENTAL

Identification of Endoplasmic Reticulum Oxidoreductin Structure and Characterization of Function Example 1

This Method Describes Construction of a Full-Length Enriched cDNA Library

An enriched full-length cDNA library can be constructed using one of two variations of the method of Carninci et al. *Genomics* 37: 327–336, 1996. These variations are based on chemical introduction of a biotin group into the diol residue of the 5' cap structure of eukaryotic mRNA to select full-length first strand cDNA. The selection occurs by trapping the biotin residue at the cap sites using streptavidin-coated magnetic beads followed by RNase I treatment to eliminate incompletely synthesized cDNAs. Second strand cDNA is synthesized using established procedures such as those provided in Life Technologies' (Rockville, Md.) "Super-Script Plasmid System for cDNA Synthesis and Plasmid Cloning" kit. Libraries made by this method have been shown to contain 50% to 70% full-length cDNAs.

The first strand synthesis methods are detailed below. An asterisk denotes that the reagent was obtained from Life Technologies, Inc.

A. First Strand cDNA Synthesis Method (with Trehalose)

| mRNA (10 ug) | 25 μl |
|---|---|
| *Not I primer (5 ug) | 10 μl |
| *5× 1st strand buffer | 43 μl |
| *0.1m DTT | 20 μl |
| *dNTP mix 10 mm | 10 μl |
| BSA 10 ug/μl | 1 μl |
| Trehalose (saturated) | 59.2 μl |
| RNase inhibitor (Promega) | 1.8 μl |
| *Superscript II RT 200 u/μl | 20 μl |
| 100% glycerol | 18 μl |
| Water | 7 μl |

The mRNA and Not I primer are mixed and denatured at 65° C. for 10 min. They are then chilled on ice and other components added to the tube. Incubation is at 45° C. for 2 min. Twenty microliters of RT (reverse transcriptase) is added to the reaction and start program on the thermocycler (MJ Research, Waltham, Mass.):

| Step 1 | 45° C. 10 min |
|---|---|
| Step 2 | 45° C. −0.3° C./cycle, 2 seconds/cycle |
| Step 3 | go to 2 for 33 cycles |
| Step 4 | 35° C. 5 min |
| Step 5 | 45° C. 5 min |
| Step 6 | 45° C. 0.2° C./cycle, 1 sec/cycle |
| Step 7 | go to 7 for 49 cycles |
| Step 8 | 55° C. 0.1° C./cycle, 12 sec/cycle |
| Step 9 | go to 8 for 49 cycles |
| Step 10 | 55° C. 2 min |
| Step 11 | 60° C. 2 min |
| Step 12 | go to 11 for 9 times |
| Step 13 | 4° C. forever |
| Step 14 | end |

B. First Strand cDNA Synthesis Method 2

| mRNA (10 μg) | 25 μl |
|---|---|
| water | 30 μl |
| *Not I adapter primer (5 μg) | 10 μl |
| 65° C. for 10 min, chill on ice, then add following reagents, | |
| *5× first buffer | 20 μl |
| *0.1M DTT | 10 μl |
| *10 mM dNTP mix | 5 μl |

Incubate at 45° C. for 2 min, then add 10 μl of *Superscript II RT (200 u/μl), start the following program:

| Step 1 | 45° C. for 6 sec, −0.1° C./cycle |
|---|---|
| Step 2 | go to 1 for 99 additional cycles |
| Step 3 | 35° C. for 5 min |
| Step 4 | 45° C. for 60 min |
| Step 5 | 50° C. for 10 min |
| Step 6 | 4° C. forever |
| Step 7 | end |

After the 1st strand cDNA synthesis, the DNA is extracted by phenol according to standard procedures, and then precipitated in NaOAc and ethanol, and stored in −20° C.

C. Oxidization of the Diol Group of mRNA for Biotin Labeling

First strand cDNA is spun down and washed once with 70% EtOH. The pellet resuspended in 23.2 μl of DEPC treated water and put on ice. Prepare 100 mM of NaIO4 freshly, and then add the following reagents:

| | |
|---|---|
| mRNA:1st cDNA (start with 20 μg mRNA) | 46.4 μl |
| 100 mM NaIO4 (freshly made) | 2.5 μl |
| NaOAc 3M pH 4.5 | 1.1 μl |

To make 100 mM NaIO4, use 21.39 μg of NaIO4 for 1 μl of water.

Wrap the tube in a foil and incubate on ice for 45 min.

After the incubation, the reaction is then precipitated in:

| | |
|---|---|
| 5M NaCl | 10 μl |
| 20% SDS | 0.5 μl |
| isopropanol | 61 μl |

Incubate on ice for at least 30 min, then spin it down at max speed at 4° C. for 30 min and wash once with 70% ethanol and then 80% EtOH.

D. Biotinylation of the mRNA Diol Group

Resuspend the DNA in 110 μl DEPC treated water, then add the following reagents:

| | |
|---|---|
| 20% SDS | 5 μl |
| 2M NaOAc pH 6.1 | 5 μl |
| 10 mm biotin hydrazide (freshly made) | 300 μl |

Wrap in a foil and incubate at room temperature overnight.

E. RNase I Treatment

Precipitate DNA in:

| | |
|---|---|
| 5M NaCl | 10 μl |
| 2M NaOAc pH 6.1 | 75 μl |
| biotinylated mRNA:cDNA | 420 μl |
| 100% EtOH (2.5 Vol) | 1262.5 μl |

(Perform this precipitation in two tubes and split the 420 μl of DNA into 210 μl each, add 5 μl of 5M NaCl, 37.5% of 2M NaOAc pH 6.1, and 631.25 μl of 100% EtOH).

Store at −20° C. for at least 30 min. Spin the DNA down at 4° C. at maximal speed for 30 min. and wash with 80% EtOH twice, then dissolve DNA in 70 μl RNase free water. Pool two tubes and end up with 140 μl.

Add the following reagents:

| | |
|---|---|
| RNase One 10 U/μl | 40 μl |
| 1st cDNA:RNA | 140 μl |
| 10× buffer | 20 μl |

Incubate at 37° C. for 15 min.

Add 5 μl of 40 μg/μl yeast tRNA to each sample for capturing.

F. Full length 1st cDNA Capturing

Blocking the beads with yeast tRNA:

| | |
|---|---|
| Beads | 1 ml |
| Yeast tRNA 40 μg/μl | 5 μl |

Incubate on ice for 30 min with mixing, wash 3 times with 1 ml of 2M NaCl, 50 mm EDTA, pH 8.0.

Resuspend the beads in 800 μl of 2M NaCl, 50 mm EDTA, pH 8.0, add RNase I treated sample 200 μl, and incubate the reaction for 30 min at room temperature.

Capture the beads using the magnetic stand, save the supernatant, and start following washes:

2 washes with 2M NaCl, 50 mm EDTA, pH 8.0, 1 ml each time, 1 wash with 0.4% SDS, 50 μg/ml tRNA, 1 wash with 10 mm Tris-Cl pH 7.5, 0.2 mm EDTA, 10 mm NaCl, 20% glycerol, 1 wash with 50 μg/ml tRNA, 1 wash with 1st cDNA buffer G. Second Strand cDNA Synthesis Resuspend the beads in:

| | |
|---|---|
| *5× first buffer | 8 μl |
| *0.1 mM DTT | 4 μl |
| *10 mm dNTP mix | 8 μl |
| *5× 2nd buffer | 60 μl |
| *E. coli Ligase 10 U/μl | 2 μl |
| *E. coli DNA polymerase 10 U/μl | 8 μl |
| *E. coli RNaseH 2 U/μl | 2 μl |
| P32 dCTP 10 μci/μl | 2 μl |
| Or water up to 300 μl | 208 μl |

Incubate at 16° C. for 2 hr with mixing the reaction in every 30 min.

Add 4 μl of T4 DNA polymerase and incubate for additional 5 min at 16° C.

Elute 2nd cDNA from the beads.

Use a magnetic stand to separate the 2nd cDNA from the beads, then resuspend the beads in 200 μl of water, and then separate again, pool the samples (about 500 μl), Add 200 μl of water to the beads, then 200 μl of phenol:chloroform, vortex, and spin to separate the sample with phenol.

Pool the DNA together (about 700 μl) and use phenol to clean the DNA again, DNA is then precipitated in 2 μg of glycogen and 0.5 vol of 7.5M NH4OAc and 2 vol of 100% EtOH.

Precipitate overnight. Spin down the pellet and wash with 70% EtOH, air-dry the pellet.

| | | | |
|---|---|---|---|
| DNA | 250 μl | DNA | 200 μl |
| 7.5M NH4OAc | 125 μl | 7.5M NH4OAc | 100 μl |
| 100% EtOH | 750 μl | 100% EtOH | 600 μl |
| glycogen 1 μg/μl | 2 μl | glycogen 1 μg/μl | 2 μl |

H. Sal I Adapter Ligation

Resuspend the pellet in 26 µl of water and use 1 µl for TAE gel.

Set up reaction as following:

| | |
|---|---|
| 2nd strand cDNA | 25 µl |
| *5× T4 DNA ligase buffer | 10 µl |
| *Sal I adapters | 10 µl |
| *T4 DNA ligase | 5 µl |

Mix gently, incubate the reaction at 16° C. overnight.

Add 2 µl of ligase second day and incubate at room temperature for 2 hrs (optional).

Add 50 µl water to the reaction and use 100 µl of phenol to clean the DNA, 90 µl of the upper phase is transferred into a new tube and precipitate in:

| | |
|---|---|
| Glycogen 1 µg/µl | 2 µl |
| Upper phase DNA | 90 µl |
| 7.5M NH4OAc | 50 µl |
| 100% EtOH | 300 µl | precipitate at −20° C. overnight

Spin down the pellet at 4° C. and wash in 70% EtOH, dry the pellet.

I. Not I Digestion

| | |
|---|---|
| 2nd cDNA | 41 µl |
| *Reaction 3 buffer | 5 µl |
| *Not I 15 u/µl | 4 µl |

Mix gently and incubate the reaction at 37° C. for 2 hr.

Add 50 µl of water and 100 µl of phenol, vortex, and take 90 µl of the upper phase to a new tube, then add 50 µl of NH4OAc and 300 µl of EtOH. Precipitate overnight at −20° C.

Cloning, ligation, and transformation are performed per the Superscript cDNA synthesis kit.

Optionally, a full length enriched cDNA library need not be used. The libraries utilized may be standard (not full length enriched) cDNA libraries known in the art. Full length sequences may be determined by joining clones containing contiguous sequences. Applicants obtained clones from the following libraries, which clones were sequenced to determine the full length or near full length sequences of the present invention. The libraries were developed from the tissue as indicated.

| Clone | Tissue |
|---|---|
| *Maize* | |
| cen1.pk0030.a10 | Endosperm |
| cen3n.pk0120.e12 | Endosperm |
| cen3n.pk0145.b10 | Endosperm |

-continued

| Clone | Tissue |
|---|---|
| cpj1c.pk009.c16 | Callus, Cells |
| cpl1c.pk003.p19 | Callus, Cells |
| cpl1c.pk009.n9 | Callus, Cells |
| cr1n.pk0092.h2 | Seedling, Root |
| p0014.ctusv72r | Leaf |
| p0042.cspao89r | Seedling, Leaf |
| p0058.chpba84r | Callus, Cells, Meristem |
| p0083.cldca66r | Kernel |
| p0090.cspsd38r | Seedling, Leaf |
| p0090.cspsd39r | Seedling, Leaf |
| p0096.cnamc39r | Seedling, Scutellum |
| p0102.cerax05r | Tassel |
| p0125.czaag02r | Tassel, Anthers |
| *Glycine Max* | |
| sgs1c.pk002.o16 | Seeds |
| sgs3c.pk001.n12 | Seeds, 25 hrs after germination |
| *Triticum aestivum* | |
| wdk2c.pk009.e11 | developing kernel, 7 days after anthesis. |
| wdk3c.pk024.o12 | developing kernel, 14 days after anthesis. |
| wr1.pk0076.f6 | root; 7 day old seedling, light grown |
| wr1.pk0106.c1 | root; 7 day old seedling, light grown |
| wre1n.pk175.e11 | root |
| wre1n.pk178.h5 | root |
| *Chyrsobalanus icaco* | |
| eci1c.pk004.j3 | developing seeds that accumulate large amounts of keto fatty acids and fatty acids with conjugated double bonds. |
| *Eucalyptus tereticornis* | |
| eec1c.pk002.f11 | older flowers, lost stamens, possibly fertilized |
| *Buthotus judaicus* | |
| ibj1c.pk007.b7 | Telsons, 48 hrs post milking |
| Chicken | |
| pnf-b.pk0010.b2 | poultry normal fat |

Example 2 cDNA Sequencing and Library Subtraction

Individual colonies can be picked and DNA prepared either by PCR with M13 forward primers and M13 reverse primers, or by plasmid isolation. cDNA clones can be sequenced using M13 reverse primers.

cDNA libraries are plated out on 22×22 cm² agar plate at density of about 3,000 colonies per plate. The plates are incubated in a 37° C. incubator for 12–24 hours. Colonies are picked into 384-well plates by a robot colony picker, Q-bot (GENETIX Limited). These plates are incubated overnight at 37° C. Once sufficient colonies are picked, they are pinned onto 22×22 cm² nylon membranes using Q-bot. Each membrane holds 9,216 or 36,864 colonies. These membranes are placed onto an agar plate with an appropriate antibiotic. The plates are incubated at 37° C. overnight.

After colonies are recovered on the second day, these filters are placed on filter paper prewetted with denaturing solution for four minutes, then incubated on top of a boiling water bath for an additional four minutes. The filters are then placed on filter paper prewetted with neutralizing solution for four minutes. After excess solution is removed by placing the filters on dry filter papers for one minute, the colony side of the filters is placed into Proteinase K solution, incubated at 37° C. for 40–50 minutes. The filters are placed on dry filter papers to dry overnight. DNA is then cross-linked to nylon membrane by UV light treatment.

Colony hybridization is conducted as described by Sambrook, J., Fritsch, E. F. and Maniatis, T., (in Molecular Cloning: A laboratory Manual, $2^{nd}$ Edition). The following probes can be used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire maize sequence database.
4. A Sal-A20 oligo nucleotide: TCG ACC CAC GCG TCC GAA AAA AAA AAA AAA AAA AAA (SEQ ID NO: 11), removes clones containing a poly A tail but no cDNA.

The image of the autoradiography is scanned into computer and the signal intensity and cold colony addresses of each colony is analyzed. Re-arraying of cold-colonies from 384 well plates to 96 well plates is conducted using Q-bot.

Example 3

Identification of the Gene from a Computer Homology Search

Gene identities are determined by conducting BLAST 2.0 (Basic Local Alignment Search Tool; Altschul, S. F., et al., (1993) *J. Mol. Biol.* 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences are analyzed for similarity to all publicly available DNA sequences contained in the "nr" database using the BLASTN algorithm. The DNA sequences are translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, as with Seq. Id. No. 9 herein, the sequencing data from two or more clones containing overlapping segments of DNA is used to construct contiguous DNA sequences.

Sequence alignments and percent identity calculations can be performed using the Megalign program of the LASERGENE bioinformatics computing suite (DNASTAR Inc., Madison, Wis.). Multiple alignment of the sequences can be performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

Example 4

Functional Characterization

An array of plants mutated to contain altered starchy phenotype and/or transgenically modified to contain polypeptides bearing multiple disulfide-bridge forming cysteines were analyzed using a proprietary transcript profiling method that compares transcript patterns in two samples. This method was developed by CuraGen® (New Haven, Conn.—See U.S. Pat. Nos. 6,141,657; 5,972,693 and 5,871,697), and hereby incorporated by reference. Fluorescently-tagged, PCR amplified cDNA fragments representing expressed transcripts can be visualized as bands or peaks on a gel tracing, and the cDNA from differentially modulated (induced or suppressed) bands can be recovered from a duplicate gel, cloned and sequenced. Known cDNAs can be identified without the need for cloning by matching the predicted size and partially known sequence of specific bands on the tracing to the sequences in database.

The kernel RNA samples from dissected 25DAP endosperm samples from 9 lines were analyzed. Eight of the lines are the kernel opacity mutant lines in the same isogenic W64A background (BC6) and one wild-type W64A line:

| # | Line | Phenotype |
|---|------|-----------|
| 1 | W64A | vitreous |
| 2 | W64A-o1 | opaque |
| 3 | W64A-o2 | opaque |
| 4 | W64A-o5 | opaque |
| 5 | W64A-o9 | opaque |
| 6 | W64A-o11 | opaque |
| 7 | W64A-Mc | opaque |
| 8 | W64A-DeB30 | opaque |
| 9 | W64A-fl2 | opaque |

In addition to this set of samples, W64A-o2 with an opaque phenotype was compared with a Quality Protein Maize (QPM) line with a vitreous phenotype. QPM is described in Quality-Protein Maize, 1998. National Research Council, National Academy Press, Washington, D.C. Recombinant inbred lines exhibiting varying levels of opacity were developed from a cross between W64A-o2 and the QPM line in Sample 11. An analysis of these lines showed a similar up regulation of endoplasm reticulum oxidoreductin in opacity mutants.

| # | Line | Phenotype |
|---|------|-----------|
| 10 | W64A-o2 | opaque |
| 11 | QPM | vitreous |

RNA was extracted from the corn seed by TriPure Isolation Reagent as suggested by manufacturer (Roche Molecular Biochemicals, Germany). The RNAs were submitted for CuraGen® transcript profiling to detect cDNA fragments that were modulated in the plants exhibiting an altered kernel opacity characteristic. In the resulting gel tracing, fragment 186.8 was identified as being up-regulated in the opaque lines (see FIG. 1 and Table 1).

Table 1: Fragments of Endoplasmic Reticulum Oxidoreductin (ERO) Gene and its Modulation in the Comparisons of Wild-Type Line Versus Mutant Lines

| Gene | | W64A vs | | | | | | | | |
|---|---|---|---|---|---|---|---|---|---|---|
| ID | Band Id | o1 | o2 | o5 | o9 | o11 | fl2 | Mc | DeB30 | All |
| ERO | 186.8 | −1.3 | −1.61 | −2.01 | −2.1 | −1.3 | −4.08 | −2.49 | −3.43 | −2.31 |

Fragment 186.8 was isolated from a gel containing a sample from the W64A-fl2 mutant. Sequence analysis of 186.8 was performed and sequence identity to a corn homologue of endoplasmic reticulum oxidoreductin was observed. By using primers to fragment 186.8 in competitive PCR, the identity of the fragment as an endoplasmic reticulum oxidoreductin specific sequence was confirmed in the W64A-fl2 opacity mutant by its removal from the gel tracing (see FIG. 2). The level of endoplasmic reticulum oxidoreductin RNA in wild type corn was significantly lower than in the W64A-fl2 mutant as was observed in both transcript profiling and competitive PCR traces (see the top graph in FIG. 1 and FIG. 2, respectively)

Subsequent analysis shown in Table 2 identified three other corn endoplasmic reticulum oxidoreductin fragments (78.6, 301.4 and 333.3) that were up-regulated in the plants with altered kernel opacity characteristic.

Table 2: Fragments of Endoplasmic Reticulum Oxidoreductin (ERO) Gene and its Modulation in the Comparisons of Wild-Type Line Versus Mutant Lines

| Gene | Band | W64A vs | | | | | | | | QPM vs |
|---|---|---|---|---|---|---|---|---|---|---|
| ID | Id | o1 | o2 | o5 | o9 | o11 | fl2 | Mc | DeB30 | o2 |
| ERO | 78.6 | −1.5 | NA* | NA* | NA* | NA* | −3.5 | −1.93 | −3.3 | NA* |
| ERO | 301.4 | NA* | −1.6 | NA* | −1.4 | −1.4 | −2.17 | −1.76 | −1.78 | NA* |
| ERO | 333.3 | NA* | NA* | NA* | NA* | NA* | −1.91 | −1.5 | −1.4 | −2.11 |

*data are not available

Sequence analysis of these fragments was performed and sequence identity to corn endoplasmic reticulum oxidoreductin was also observed. The gel tracing showing the up-regulation of 301.4 is shown in FIG. 3, and the gel tracing confirming band 301.4 as an endoplasmic reticulum oxidoreductin via competitive PCR is shown in FIG. 4.

In summary, corn endoplasmic reticulum oxidoreductin was shown in both Table 1 and Table 2 as highly induced in the opaque lines, and in particular, W64A-Mc, W64A-fl2 and W64A-DeB30. At least one fragment of endoplasmic reticulum oxidoreductin (fragment 333.3) was detected and confirmed to be modulated in comparison of QPM vs W64A-o2, where QPM is a line with restored, vitreous kernel phenotype.

Thus, applicants have shown that the transcript for endoplasmic reticulum oxidoreductin is up-regulated in the maize kernel opacity mutants, and this demonstrates the functional importance of endoplasmic reticulum oxidoreductin in protein folding, the formation of the seed starch-protein matrix, and the maize unfolded protein response Additional data shows that protein disulfide isomerase may also be up-regulated simultaneously and in the same direction as endoplasmic reticulum oxidoreductin.

Example 5

Transformation and Regeneration of Transgenic Maize Plants

Immature maize embryos from greenhouse donor plants are bombarded with a plasmid containing an endoplasmic reticulum oxidoreductin nucleotide sequence operably linked to a 27 kD gamma zein promoter, a corn globulin 1 promoter or a phaseolin promoter, plus a pin II terminator (An et. al. 1989) if desired, plus a selectable marker gene such as the PAT gene (Wohlleben et al. (1988) Gene 70:25–37) that confers resistance to the herbicide Bialaphos. Transformation is performed as follows. Media recipes follow below.

Transformation of Maize

Freshly isolated immature embryos of maize, about 10 days after pollination (DAP), are cultured for 4–5 days before transforming DNA is delivered via particle bombardment. The preferred genotype for transformation is the highly transformable genotype Hi-II (Armstrong, C. L., 1991, Development and Availability of Germplasm with High Type II Culture Formation Response, Maize Genetics Cooperation Newsletter, 65:92–93). An $F_1$ hybrid created by crossing with a Hi-II with an elite inbred may also be used. After DNA delivery, the embryos are cultured on medium containing toxic levels of herbicide. Only those cells which receive the herbicide-resistance gene, and the linked gene(s), grow on selective medium. Transgenic events so selected are propagated and regenerated to whole plants, produce seed, and transmit transgenes to progeny.

Particle Gun Terminology and Use

The PDS-1000 Biolistics particle bombardment device is used to transform maize. The operation of this device is detailed in the operating instructions available from the manufacturer (Bio-Rad Laboratories, Hercules, Calif.).

The macrocarrier flight distance is fixed in the instrument at ¼" (0.25"). While the rupture disk-macrocarrier gap distance is adjustable, the device is operated at the factory recommended distance of ⅛" (0.125").

Preparation of Particles

The transforming DNA is associated with either tungsten or gold particles. Prior to association with the transforming DNA, the tungsten particles are prepared essentially as described by Tomes et al. (U.S. Pat. No. 5,990,387).

The preferred method utilizes gold particles. Gold particles are prepared as follows. Sixty mg of 0.6μ gold particles (Bio-Rad) are placed in 2.0 mL Sarstedt tube. The particles are washed three times in absolute ethanol (100%). Each ethanol wash involves adding one mL of absolute ethanol to the tube, sonicating the tube briefly, vortexing the tube on high for one minute, centrifuging the tube to pellet the particles and discarding the supernatant. The particles are then washed two times in sterile deionized water. Each wash involves adding one mL of sterile deionized water to the tube, sonicating the tube briefly, vortexing the tube on high for one minute, centrifuging the tube to pellet the particles and discarding the supernatant. Following the ethanol and water wash steps, one mL of sterile deionized water is added to the tube and the tube is sonicated. Aliquots (250 μL) of the particle-containing suspension are removed to siliconized 1.5 mL tubes and combined with 750 μL sterile deionized water.

Association of Particles with Transforming DNA

The transforming DNA is associated with the prepared tungsten or gold particles by precipitation in a solution comprising $CaCl_2$ and spermidine as follows. A tube containing tungsten or gold particles prepared as described above is sonicated for 3 seconds at setting 2.5 in a water bath probe, Branson Sonicator #450 (Branson Ultrasonics Corp., Danbury Conn.). Ten μL plasmid DNA (1 μg plasmid total) in TE buffer is added to the tube and mixed for 5 seconds. Next, 100 μL 2.5 M $CaCl_2$ and 10 μL 0.1 M spermidine are added. The tube is then shaken on a vortexer for 10 minutes followed by centrifugation for 30 seconds at 10,000 rpm. The supernatant is removed and discarded, and 500 μL absolute ethanol is added. The tube is then sonicated at setting 2.5 for 3 seconds, centrifuged for 30 seconds at 10,000 rpm and the supernatant removed. To the tube, 105 μL of absolute ethanol is added. The tube is sonicated for 3 seconds at setting 2.5 before placing a 10 μL aliquot onto the center of a macrocarrier.

Preparation of Target Tissue

Ears of Hi-II or Hi-II X elite inbred are sampled in planta to assess the developmental stage of the embryos. When immature embryos first become opaque, about 9–12 days post-pollination, the ears are harvested for embryo dissection. The embryos are approximately 1.5–1.8 mm long from coleoptilar to coleorhizal end. Immature embryos are the target tissue for transient and stable transformation experiments.

The ears are surface sterilized in 50% (v/v) Clorox bleach+0.5% (v/v) Micro detergent for 20 minutes, and then rinsed twice with sterile water. The immature embryos are excised from the caryopsis and placed embryo axis side down (scutellum side up) onto transformation support medium.

Embryos are cultured on 560 L medium for 4–5 days in darkness at 28° C. At this time, a small amount of incipient embryogenic tissue can be observed at the coleorhizal end of the scutellum, but there is no production of subculturable tissue.

Delivery of DNA

As preparation for bombardment, the 4 day pre-cultured embryos are transferred to 561Y medium, which contains elevated sucrose, and are incubated in darkness at 28° C. for 4 hours. The embryos are arranged, 10 embryos per plate, in a 2 cm target area. The embryos are angled with their coleorhizal end pointing up toward the macrocarrier at approximately a 30° angle. This orientation of the cultured embryos enhances exposure of the preferred cell targets to the path of particles propelled by the particle gun. Plates of embryos are bombarded at shelf 2 from the bottom of the device, 650 PSI rupture disk, and a chamber vacuum of 28 mm Hg.

The bombarded plates are incubated in darkness at 28° C. for two days. After the two-day bombardment recovery period, the embryos are transferred to Petri dishes containing 560 R medium. This latter medium is comprised of those components which typically are used to initiate and promote embryogenic tissue from maize embryos, and contains 2% sucrose, and 3 ppm bialaphos as a selective agent. The plates are incubated in darkness at 28° C. for 4–6 weeks, or until growth of putatively transformed events are observed. 560 R culture medium does not support the growth of untransformed tissue derived from the bombarded embryos. Therefore, only putatively transformed tissue, resistant to bialaphos as a consequence of expressing the resistance transgene, are competent to grow.

Putatively transformed events are identified first by their growth under selective conditions and individually subcultured to fresh 560 R medium for propagation. Samples of each event are assayed for their transgenic nature by PCR reaction using primer sets designed to specifically amplify sequences in the inserted gene(s).

Regeneration of $T_0$ Plants

Transformed, selection-resistant embryogenic tissue is transferred to 288 J medium to initiate plant regeneration. Following somatic embryo maturation (2–4 weeks), well-developed somatic embryos are transferred to medium for germination (272 V) and transferred to a lighted culture room. Approximately 7–10 days later, developing plantlets are transferred to 272 V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to 1.6 gallon pots and grown to maturity. Plants are monitored and scored for altered endoplasmic reticulum oxidoreductin and/or phenotype such as altered starch-protein matrix or protein characteristics indicative of altered oxidative conditions in the endoplasmic reticulum. Endoplasmic reticulum oxidoreductin may be assayed as described in Coughlan, et. al., (1996), Molecular Characterization of Plant Endoplasmic Reticulum, Identification of Protein Disulfide Isomerase as the Major Reticuloplasmin., Eur. J. Biochem., 235:215–224.

Media Recipes

Medium 288 J contains the following ingredients: 950.000 ml of D-I $H_2O$; 4.300 g of MS Salts; 0.100 g of Myo-Inositol; 5.000 ml of MS Vitamins Stock Solution (No. 36J); 1.000 ml of Zeatin .5 mg/ml; 60.000 g of Sucrose; 3.000 g of Gelrite, which is added after Q.S. to volume; 2.000 ml of IAA 0.5 mg/ml #; 1.000 ml of 0.1 Mm ABA #; 3.000 ml of Bialaphos 1 mg/ml #; and 2.000 ml of Agribio Carbenicillin 50 mg/ml #. Directions are: dissolve ingredients in polished D-I $H_2O$ in sequence; adjust to pH 5.6; Q.S. to volume with polished D-I $H_2O$ after adjusting pH; sterilize and cool to 60° C. Add 3.5 g/L of Gelrite for cell biology. Ingredients designated with # are added after sterilizing and cooling to temperature.

Medium 272 V contains the following ingredients: 950.000 ml of D-I $H_2O$; 4.300 g of MS Salts; 0.100 g of Myo-Inositol; 5.000 ml of MS Vitamins Stock Solution;

40.000 g of Sucrose; and 6.000 g of Bactoagar, which is added after Q.S. to volume. Directions are: dissolve ingredients in polished D-I H$_2$O in sequence; adjust to pH 5.6; Q.S. to volume with polished D-I H$_2$O after adjusting pH; and sterilize and cool to 60° C.

Medium 560 L contains the following ingredients: 950.000 ml of D-I Water, Filtered; 4.000 g of CHU (N6) Basal Salts (SIGMA C-1416); 1.000 ml of Eriksson's Vitamin Mix (1000X SIGMA-1511); 1.250 ml of Thiamine.HCL 0.4 mg/ml; 30.000 g of Sucrose; 4.000 ml of 2,4-D 0.5 mg/ml; 3.000 g of Gelrite, which is added after Q.S. to volume; and 0.425 ml of Silver Nitrate 2 mg/ml #. Directions are: dissolve ingredients in D-I H$_2$O in sequence; adjust to pH 5.8 with KOH; bring up to volume with D-I H$_2$O; sterilize and cool to room temperature. Total volume (L)=1.00. Ingredients designated with # are added after sterilizing and cooling to temperature.

Medium 560 R contains the following ingredients: 950.000 ml D-I Water, Filtered; 4.000 g of CHU (N6) Basal Salts (SIGMA C-1416); 1.000 ml Eriksson's Vitamin Mix (1000X SIGMA-1511); 1.250 ml of Thiamine.HCL 0.4 mg/ml; 30.000 g Sucrose; 4.000 ml of 2,4-D 0.5 mg/ml; 3.000 g of Gelrite, which is added after Q.S. to volume; 0.425 ml of Silver Nitrate 2 mg/ml #; and 3.000 ml of Bialaphos 1 mg/ml #. Directions are: dissolve ingredients in D-I H$_2$O in sequence; adjust to pH 5.8 with KOH; bring up to volume with D-I H$_2$O; sterilize and cool to room temperature. Total volume (L)=1.00. Ingredients designated with # are added after sterilizing and cooling to temperature.

Medium 561 Y contains the following ingredients: 950.000 ml of D-I Water, Filtered; 4.000 g of CHU (N6) Basal Salts (SIGMA C-1416); 1.000 ml of Eriksson's Vitamin Mix (1000X SIGMA-1511); 1.250 ml of Thiamine.HCL 0.4 mg/ml; 190.000 g of Sucrose; 2.000 ml of 2,4-D 0.5 mg/ml; 2.880 g of L-Proline; 2.000 g of Gelrite, which is added after Q.S. to volume; and 4.250 ml of Silver Nitrate 2 mg/ml #. Directions are: dissolve ingredients in D-I H$_2$O in sequence; adjust to pH 5.8 with KOH; bring up to volume with D-I H$_2$O; sterilize and cool to room temperature. Autoclave less time because of increased sucrose. Total volume (L)=1.00. Ingredients designated with # are added after sterilizing and cooling to temperature.

Example 6

Agrobacterium-Mediated Transformation of Maize

For Agrobacterium-mediated transformation of maize with an endoplasmic reticulum oxidoreductin nucleotide sequence, a maize cDNA for an endoplasmic reticulum oxidoreductin nucleotide sequence is operably linked to a 27 kD gamma zein promoter, a corn globulin 1 promoter or a phaseolin promoter, plus a pin II terminator (An et. al. 1989) if desired. The endoplasmic reticulum oxidoreductin cassette, also containing a CaMV35S-bialaphos selectable marker element, is cloned into a binary vector and introduced into Agrobacterium.

Transformation is performed as follows. Media recipes follow below.

Transformation of Maize Mediated by Agrobacterium

Freshly isolated immature embryos of maize, about 10 days after pollination (DAP), are incubated with the Agrobacterium. The preferred genotype for transformation is the highly transformable genotype Hi-II (Armstrong, C. L., 1991, Development and Availability of Germplasm with High Type II Culture Formation Response, Maize Genetics Cooperation Newsletter, 65:92–93). An F$_1$ hybrid created by crossing with an Hi-II with an elite inbred may also be used. After Agrobacterium treatment of immature embryos, the embryos are cultured on medium containing toxic levels of herbicide. Only those cells which receive the herbicide-resistance gene, and the linked gene(s), grow on selective medium. Transgenic events so selected are propagated and regenerated to whole plants, produce seed, and transmit transgenes to progeny.

Preparation of Agrobacterium

The engineered Agrobacterium tumefaciens LBA4404 is constructed as per U.S. Pat. No. 5,591,616 to contain the linked gene(s) and the selectable marker gene. Typically either BAR (D'Halluin et al. (1992) Methods Enzymol. 216:415–426) or PAT (Wohlleben et al. (1988) Gene 70:25–37) may be used.

To use the engineered vector in plant transformation, a master plate of single bacterial colonies is first prepared by inoculating the bacteria on minimal AB medium and then incubating the bacteria plate inverted at 28° C. in darkness for about 3 days. A working plate is then prepared by selecting a single colony from the plate of minimal A medium and streaking it across a plate of YP medium. The YP-medium bacterial plate is then incubated inverted at 28° C. in darkness for 1–2 days.

Agrobacterium for plant transfection and co-cultivation is prepared 1 day prior to transformation. Into 30 ml of minimal A medium in a flask is placed 50 µg/ml spectinomycin (or appropriate bacterial antibiotic depending on marker in co-integrate),100 µM acetosyringone, and about a ⅛ loopful of Agrobacterium from a 1 to 2-day-old working plate. The Agrobacterium is then grown at 28° C. at 200 rpm in darkness overnight (about 14 hours). In mid-log phase, the Agrobacterium is harvested and resuspended at 3 to 5×10$^8$ CFU/ml in 561Q medium+100 µM acetosyringone using standard microbial techniques and standard curves.

Immature Embryo Preparation

Nine to ten days after controlled pollination of a corn plant, developing immature embryos are opaque and 1–1.5 mm long and are the appropriate size for Agro-infection. The husked ears are sterilized in 50% commercial bleach and 1 drop Tween for 30 minutes, and then rinsed twice with sterile water. The immature embryos are aseptically removed from the caryopsis and placed into 2 ml of sterile holding solution comprising of 561Q+100 µM acetosyringone.

Agrobacterium Infection and Co-cultivation of Embryos

Holding solution is decanted from excised immature embryos and replaced with prepared Agrobacterium. Following gentle mixing and incubation for about 5 minutes, the Agrobacterium is decanted from the immature embryos. Immature embryos are then moved to a plate of 562P medium, scutellum surface upwards, and incubated at 20° C. for 3 days in darkness followed by incubation at 28° C. for 3 days in darkness on medium 562P+100 mg/ml carbenecillin (see U.S. Pat. No. 5,981,840).

Selection of Transgenic Events

Following incubation, the immature embryos are transferred to 5630 medium for selection of events. The transforming DNA possesses a herbicide-resistance gene, in this example the PAT gene, which confers resistance to bialaphos. At 10- to 14-day intervals, embryos are transferred to 5630 medium. Actively growing putative transgenic embryogenic tissue are visible in 6–8 weeks.

Regeneration of $T_0$ Plants

Transgenic embryogenic tissue is transferred to 288W medium and incubated at 28° C. in darkness until somatic embryos matured, or about 10 to 18 days. Individual matured somatic embryos with well-defined scutellum and coleoptile are transferred to 272 embryo germination medium and incubated at 28° C. in the light. After shoots and roots emerge, individual plants are potted in soil and hardened-off using typical horticultural methods.

Confirmation of Transformation

Putative transgenic events are subjected to analysis to confirm their transgenic nature. Events are tested for the presence of the endoplasmic reticulum oxidoreductin by PCR amplification. Additionally, To plants are painted with bialaphos herbicide. The subsequent lack of a herbicide-injury lesion indicates the presence and action of the herbicide resistance gene. The plants are monitored and scored for altered endoplasmic reticulum oxidoreductin expression and/or phenotype such as increased organic sulfur compounds. Endoplasmic reticulum oxidoreductin may be assayed as described in Coughlan, et. al., (1996), Molecular Characterization of Plant Endoplasmic Reticulum, Identification of Protein Disulfide Isomerase as the Major Reticuloplasmin., Eur. J. Biochem., 235:215–224.

Media Recipes

Medium 561 Q contains the following ingredients: 950.000 ml of D-I Water, Filtered; 4.000 g of Chu (N6) Basal Salts (Sigma C-1416); 1.000 ml of Eriksson's Vitamin Mix (1000x Sigma-1511); 1.250 ml of Thiamine.HCL.4 mg/ml; 3.000 ml of 2,4-D 0.5 mg/ml (No. 2A); 0.690 g of L-proline; 68.500 g of Sucrose; and 36.000 g of Glucose. Directions are: dissolve ingredients in polished D-I $H_2O$ in sequence; adjust pH to 5.2 w/KOH; Q.S. to volume with polished D-I $H_2O$ after adjusting pH; and filter sterilize (do not autoclave).

Medium 562 P contains the following ingredients: 950.000 ml of D-I Water, Filtered; 4.000 g of Chu (N6) Basal Salts (Sigma C-1416); 1.000 ml of Eriksson's Vitamin Mix (1000x Sigma-1511); 1.250 ml of Thiamine.HCL.4 mg/ml; 4.000 ml of 2,4-D 0.5 mg/ml; 0.690 g of L-proline; 30.000 g of Sucrose; 3.000 g of Gelrite, which is added after Q.S. to volume; 0.425 ml of Silver Nitrate 2 mg/ml #; and 1.000 ml of Aceto Syringone 100 mM #. Directions are: dissolve ingredients in polished D-I $H_2O$ in sequence; adjust pH to 5.8 w/KOH; Q.S. to volume with polished D-I $H_2O$ after adjusting pH; and sterilize and cool to 60° C. Ingredients designated with a # are added after sterilizing and cooling to temperature.

Medium 563 O contains the following ingredients: 950.000 ml of D-I Water, Filtered; 4.000 g of Chu (N6) Basal Salts (Sigma C-1416); 1.000 ml of Eriksson's Vitamin Mix (1000x Sigma-1511); 1.250 ml of Thiamine.HCL.4 mg/ml; 30.000 g of Sucrose; 3.000 ml of 2,4-D 0.5 mg/ml (No. 2A); 0.690 g of L-proline; 0.500 g of Mes Buffer; 8.000 g of Agar (Sigma A-7049, Purified), which is added after Q.S. to volume; 0.425 ml of Silver Nitrate 2 mg/ml #; 3.000 ml of Bialaphos 1 mg/ml #; and 2.000 ml of Agribio Carbenicillin 50 mg/ml #. Directions are: dissolve ingredients in polished D-I $H_2O$ in sequence; adjust to pH 5.8 w/koh; Q.S. to volume with polished D-I $H_2O$ after adjusting pH; sterilize and cool to 60° C. Ingredients designated with a # are added after sterilizing and cooling to temperature.

Medium 288 W contains the following ingredients: 950.000 ml of D-I $H_2O$; 4.300 g of MS Salts; 0.100 g of Myo-Inositol; 5.000 ml of MS Vitamins Stock Solution (No. 36J); 1.000 ml of Zeatin.5 mg/ml; 60.000 g of Sucrose; 8.000 g of Agar (Sigma A-7049, Purified), which is added after Q.S. to volume; 2.000 ml of IAA 0.5 mg/ml #; 1.000 ml of 0.1 Mm ABA #; 3.000 ml of Bialaphos 1 mg/ml #; and 2.000 ml of Agribio Carbenicillin 50 mg/ml #. Directions are: dissolve ingredients in polished D-I $H_2O$ in sequence; adjust to pH 5.6; Q.S. to volume with polished D-I $H_2O$ after adjusting pH; sterilize and cool to 60° C. Add 3.5 g/L of Gelrite for cell biology. Ingredients designated with a # are added after sterilizing and cooling to temperature.

Medium 272 contains the following ingredients: 950.000 ml of D-I H2O; 4.300 g of MS Salts; 0.100 g of Myo-Inositol; 5.000 of MS Vitamins Stock Solution; 40.000 g of Sucrose; and 1.500 g of Gelrite, which is added after Q.S. to volume. Directions are: dissolve ingredients in polished D-I H2O in sequence; adjust to pH 5.6; Q.S. to volume with polished D-I H2O after adjusting pH; and sterilize and cool to 60° C.

Medium minimal A contains the following ingredients: 950.000 ml of D-I H2O; 10.500 g of potassium phosphate dibasic K2HPO4; 4.500 g of potassium phosphate monobasic KH2PO4; 1.000 g of ammonium sulfate; 0.500 g of sodium citrate dihydrate; 10.000 ml of sucrose 20% solution #; and 1.000 ml of 1M magnesium sulfate #. Directions are: dissolve ingredients in polished D-I H2O in sequence; Q.S. to volume with D-I H2O; sterilize and cool to 60° C. Ingredients designated with a # are added after sterilizing and cooling to temperature.

Medium minimal AB contains the following ingredients: 850.000 ml of D-I H2O; 50.000 ml of stock solution 800A; 9 g of Phytagar which is added after Q.S. to volume; 50.000 ml of stock solution 800B #; 5.000 g of glucose #; and 2.000 ml of spectinomycin 50/mg/ml stock #. Directions are: dissolve ingredients in polished D-I H2O in sequence; Q.S. to volume with polished D-I H2O less 100 ml per liter; sterilize and cool to 60° C. Ingredients designated with a # are added after sterilizing and cooling to temperature. Stock solution 800A contains the following ingredients: 950.000 ml of D-I H2O; 60.000 g of potassium phosphate dibasic $K_2HPO_4$; and 20.000 g of sodium phos. monobasic, hydrous. Directions are: dissolve ingredients in polished D-I H2O in sequence; adjust pH to 7.0 w/koh; Q.S. to volume with polished D-I H2O after adjusting pH; and sterilize and cool to 60° C. Stock solution 800B contains the following ingredients: 950.000 ml of D-I H2O; 20.000 g of ammonium chloride; 6.000 g of magnesium sulfate 7-H2O, MgSO4, 7H2O; 3.000 g of potassium chloride; 0.200 g of calcium chloride (anhydrate); and 0.050 g of ferrous sulfate 7-hydrate. Directions are: dissolve ingredients in polished D-I H2O in sequence; Q.S. to volume with polished D-I H2O; and sterilize and cool to 60° C.

Medium minimal YP contains the following ingredients: 950.000 ml of D-I H2O; 5.000 g of yeast extract (Difco); 10.000 g of peptone (Difco); 5.000 g of sodium chloride; 15.000 g of bacto-agar, which is added after Q.S. to volume; and 1.000 ml of spectinomycin 50 mg/ml stock #. Directions are: dissolve ingredients in polished D-I H2O in sequence; adjust pH to 6.8 w/koh; Q.S. to volume with polished D-I H2O after adjusting pH; sterilize and cool to 60° C. Ingredients designated with a # are added after sterilizing and cooling to temperature.

Example 7

Soybean Embryo Transformation and Regeneration of Plants

Soybean embryos are bombarded with a plasmid containing an endoplasmic reticulum oxidoreductin nucleotide sequence operably linked to a seed-preferred promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the $^{35}S$ promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the endoplasmic reticulum oxidoreductin nucleotide sequence operably linked to a seed-preferred promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

*Agrobacterium*-Mediated Transformation of Sorghum.

For *Agrobacterium*-mediated transformation of *sorghum* the method of Cai et al. can be employed (U.S. patent application Ser. No. 09/056,418), the contents of which are hereby incorporated by reference). This method can be employed with a nucleotide sequence encoding any of the proteins of the present invention using a seed specific promoter or another suitable promoter.

Example 9

Sunflower Meristem Tissue Transformation and Regeneration of Plants

Sunflower meristem tissues are transformed with an expression cassette comprising an endoplasmic reticulum oxidoreductin nucleotide sequence operably linked to a seed-preferred promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9: 55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to *Agrobacterium* treatment (Bidney et al. (1992) *Plant Mol. Biol.* 18: 301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the endoplasmic reticulum oxidoreductin nucleotide sequence operably linked to a seed-preferred promoter is introduced into *Agrobacterium* strain EHA105 via freeze-thawing as described by Holsters et al. (1978) *Mol. Gen. Genet.* 163: 181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for endoplasmic reticulum oxidoreductin activity.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of To plants (parental generation) maturing in the greenhouse are identified by NPTII ELISA while transgenic seeds harvested from NPTII-positive To plants are identified by endoplasmic reticulum oxidoreductin activity or malic enzyme activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 g/l kanamycin is resuspended in an inoculation medium (12.5 mM 2-mM 2-(N-morpholino) ethanesulfonic acid, MES, 1 g/l $NH_4Cl$ and 0.3 µl $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for endoplasmic reticulum oxidoreductin using assays known in the art. After positive (i.e., a desired level of protein expression or altered phenotype) explants are identified, those shoots that fail to exhibit the desired level of expression are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for the desired protein or phenotype are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 10

Transformation of Rice Embryogenic Callus by Bombardment

Embryogenic callus cultures derived from the scutellum of germinating seeds serve as the source material for transformation experiments. This material is generated by germinating sterile rice seeds on a callus initiation media (MS salts, Nitsch and Nitsch vitamins, 1.0 mg/l 2,4-D and 10 µM $AgNO_3$) in the dark at 27–28° C. Embryogenic callus proliferating from the scutellum of the embryos is then transferred to CM media (N6 salts, Nitsch and Nitsch vitamins, 1 mg/1 2,4-D, Chu et al., 1985, Sci. Sinica 18:659–668). Callus cultures are maintained on CM by routine sub-culture at two week intervals and used for transformation within 10 weeks of initiation.

Callus is prepared for transformation by subculturing 0.5–1.0 mm pieces approximately 1 mm apart, arranged in a circular area of about 4 cm in diameter, in the center of a circle of Whatman #541 paper placed on CM media. The plates with callus are incubated in the dark at 27–28° C. for 3–5 days. Prior to bombardment, the filters with callus are transferred to CM supplemented with 0.25 M mannitol and 0.25 M sorbitol for 3 hr. in the dark. The petri dish lids are then left ajar for 20–45 minutes in a sterile hood to allow moisture on tissue to dissipate.

Circular plasmid DNA from two different plasmids one containing the selectable marker for rice transformation and one containing the nucleotide of the invention, are co-precipitated onto the surface of gold particles. To accomplish this, a total of 10 µg of DNA at a 2:1 ratio of trait:selectable marker DNAs is added to a 50 µl aliquot of gold particles resuspended at a concentration of 60 mg ml$^{-1}$. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28–29 inches Hg. The macrocarrier is accelerated with a helium shock wave using a rupture membrane that bursts when the He pressure in the shock tube reaches 1080–1100 psi. The tissue is placed approximately 8 cm from the stopping screen and the callus is bombarded two times. Five to seven plates of tissue are bombarded in this way with the DNA-coated gold particles. Following bombardment, the callus tissue is transferred to CM media without supplemental sorbitol or mannitol.

Within 3–5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates incubated in the dark for 4 weeks at 27–28° C. After 4 weeks, transgenic callus events are identified, transferred to fresh SM plates and grown for an additional 2 weeks in the dark at 27–28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+ 50 ppm hyg B) and placed under cool white light (~40 µEm$^{-2}$s$^{-1}$) with a 12 hr photoperiod at 25° C. and 30–40% humidity. After 2–4 weeks in the light, callus generally begins to organize, and form shoots. Shoots are removed from surrounding callus/media and gently transferred to RM3 media (½× MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2–3 weeks, when sufficient root and shoot growth has occurred. Plants are grown using a 12 hr/12 hr light/dark cycle using ~30/18° C. day/night temperature regimen.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid comprising a polynucleotide selected from the group consisting of:
   a) a polynucleotide encoding the polypeptide of SEQ ID NO: 2; and
   b) the polynucleotide of SEQ ID NO: 1.

2. A recombinant expression cassette, comprising the nucleic acid of claim 1 operably linked to a promoter.

3. The recombinant expression cassette of claim 2, wherein the promoter is selected from the group consisting of a 27 kD gamma zein promoter, a corn globulin 1 promoter and a phaseolin promoter.

4. A plant cell comprising the recombinant expression cassette of claim 2.

5. A transgenic plant comprising the recombinant expression cassette of claim 2.

6. The transgenic plant of claim 5, wherein said plant is a monocot.

7. The transgenic plant of claim 5, wherein said plant is a dicot.

8. The transgenic plant of claim 5, wherein said plant is selected from the group consisting of maize, soybean, sunflower, sorghum, safflower, canola, wheat, alfalfa, cotton, rice, barley, and millet.

9. A transgenic seed from the transgenic plant of claim 8.

10. A method of increasing the level of endoplasmic reticulum oxidoreductin protein in a maize plant cell, wherein the method comprises:
   a) introducing into a maize plant cell a recombinant expression cassette comprising the polynucleotide of claim 1 operably linked to a promoter;
   b) culturing the maize plant cell; and
   c) permitting expression of said polynucleotide for a time sufficient to increase the level of endoplasmic reticulum oxidoreductin protein in said plant cell.

* * * * *